(12) United States Patent
Yokoyama et al.

(10) Patent No.: US 9,634,258 B2
(45) Date of Patent: Apr. 25, 2017

(54) COMPOUNDS HAVING BIPYRIDYL GROUP AND CARBAZOLE RING, AND ORGANIC ELECTROLUMINESCENT ELEMENT

(75) Inventors: Norimasa Yokoyama, Tokyo (JP); Naoaki Kabasawa, Tokyo (JP); Musubu Ichikawa, Nagano (JP); Sohei Otsuru, Nagano (JP)

(73) Assignees: HODOGAYA CHEMICAL CO., LTD., Tokyo (JP); SHINSHU UNIVERSITY, Matsumoto-shi (JP)

( * ) Notice: Subject to any disclaimer, the term of this patent is extended or adjusted under 35 U.S.C. 154(b) by 782 days.

(21) Appl. No.: 14/001,580

(22) PCT Filed: Feb. 24, 2012

(86) PCT No.: PCT/JP2012/054530
§ 371 (c)(1),
(2), (4) Date: Aug. 26, 2013

(87) PCT Pub. No.: WO2012/115219
PCT Pub. Date: Aug. 30, 2012

(65) Prior Publication Data
US 2013/0328041 A1    Dec. 12, 2013

(30) Foreign Application Priority Data
Feb. 25, 2011    (JP)  ................ 2011-039406

(51) Int. Cl.
H01L 51/54    (2006.01)
C09K 11/06    (2006.01)
(Continued)

(52) U.S. Cl.
CPC ........ H01L 51/0067 (2013.01); C07D 401/14 (2013.01); C09B 57/00 (2013.01);
(Continued)

(58) Field of Classification Search
CPC .... C07D 401/00; C07D 401/14; C09K 11/06; C09K 2211/1018; C09K 2211/1007; C09K 2211/1011; C09K 2211/1029; H01L 51/0032; H01L 51/0062; H01L 51/0067; H01L 51/0071; H01L 51/0072; H01L 51/50; H01L 51/5012; H01L 51/5016; H01L 51/5096; H05B 33/14
USPC ....... 428/690, 691, 917, 411.4, 336; 427/58, 427/66; 313/500–512; 257/40, 88–104, 257/E51.001–E51.052; 252/301.16–301.35; 546/256
See application file for complete search history.

(56) References Cited

U.S. PATENT DOCUMENTS

2009/0021146 A1   1/2009   Iida et al.
2009/0045726 A1   2/2009   Miki et al.
(Continued)

FOREIGN PATENT DOCUMENTS

JP         2004071380 A  *   3/2004
JP   WO 2006080229 A1  *   8/2006  ........... C07D 209/86
(Continued)

OTHER PUBLICATIONS

Machine translation of JP2004-071380. Date of publication: Mar. 4, 2004.*
(Continued)

*Primary Examiner* — Andrew K Bohaty
(74) *Attorney, Agent, or Firm* — Oblon, McClelland, Maier & Neustadt, L.L.P.

(57) ABSTRACT

The present invention relates to a compound having a bipyridyl group and a carbazole ring, which is represented by the following general formula (1); and an organic electroluminescent element containing a pair of electrodes and at least one organic layer interposed therebetween, in which the compound is used as a constituent material of the at least one organic layer:

[Chem. 1]

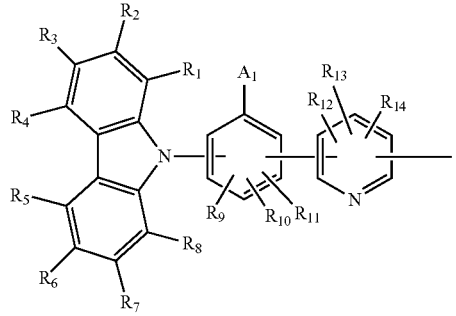

(1)

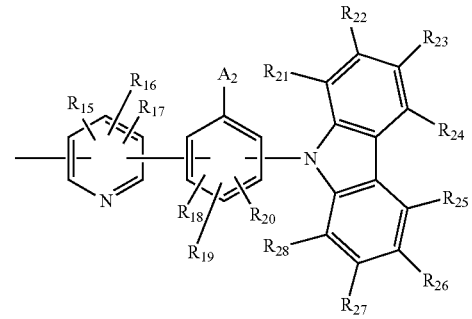

64 Claims, 2 Drawing Sheets

(51) Int. Cl.
*H01L 51/00* (2006.01)
*H05B 33/14* (2006.01)
*C07D 401/14* (2006.01)
*C09B 57/00* (2006.01)
*H01L 51/50* (2006.01)

(52) U.S. Cl.
CPC .......... *C09K 11/06* (2013.01); *H01L 51/0072* (2013.01); *H05B 33/14* (2013.01); *C09K 2211/1007* (2013.01); *C09K 2211/1011* (2013.01); *C09K 2211/1029* (2013.01); *H01L 51/5012* (2013.01); *H01L 51/5096* (2013.01)

(56) References Cited

U.S. PATENT DOCUMENTS

| | | | |
|---|---|---|---|
| 2010/0213452 A1 | 8/2010 | Sisk et al. | |
| 2010/0213453 A1 | 8/2010 | Sisk et al. | |
| 2010/0213829 A1 | 8/2010 | Sisk et al. | |
| 2010/0213830 A1 | 8/2010 | Sisk et al. | |
| 2010/0213831 A1 | 8/2010 | Sisk et al. | |
| 2010/0213832 A1 | 8/2010 | Sisk et al. | |

FOREIGN PATENT DOCUMENTS

| | | |
|---|---|---|
| JP | 2006 232813 | 9/2006 |
| JP | 2007 22986 | 2/2007 |
| JP | 4474493 | 6/2010 |
| WO | 2007 069607 | 6/2007 |
| WO | 2010 090925 | 8/2010 |
| WO | WO 2011/013843 A1 | 2/2011 |

OTHER PUBLICATIONS

Extended European Search Report issued on Jun. 20, 2014 in the corresponding European Application No. 12749183.5.

Agata, Y., et al., "Syntheses and Properties of Novel Quarterphenylene-based Materials for Blue Organic Light-emitting Devices", Chemistry Letters, vol. 36, No. 2, pp. 316-317, (2007).

Jeon, J.Y., et al., "Bipolar Host Materials for Green Triplet Emitter in Organic Light-emitting Diodes", Chemistry Letters, vol. 36, No. 9, pp. 1156-1157, (2007).

Baldo, M.A., et al., "Very high-efficiency green organic light-emitting devices based on electrophosphorescence", vol. 75, No. 1, pp. 4-6, (Jul. 5, 1999).

"Development and Evaluation Technology of Materials for Organic EL illumination", Science &Technology Co., Ltd.A, pp. 102-106, (2010).

"Organic EL displays", OHMSHA, p. 90, (2005).

"Proceedings of the First Meeting", Conferences on Organic EL, vol. 19, pp. 19-20, (2005) (with partial English translation).

International Search Report Issued Apr. 10, 2012 in PCT/JP12/054530 Filed Feb. 24, 2012.

* cited by examiner

COMPOUNDS HAVING BIPYRIDYL GROUP AND CARBAZOLE RING, AND ORGANIC ELECTROLUMINESCENT ELEMENT

CROSS REFERENCE TO RELATED APPLICATIONS

The present application is a 35 U.S.C.§371 national stage patent application of International patent application PCT/JP2012/054530, filed on Feb. 24, 2012, published as WO/2012/115219 on Aug. 30, 2012, the text of which is incorporated by reference, and claims the benefit of the filing date of Japanese application no. 2011-039406, filed on Feb. 25, 2011, the text of which is also incorporated by reference.

TECHNICAL FIELD

The present invention relates to a compound suited for an organic electroluminescent element which is a self-light-emitting element suited for use in various display devices; and such an element. More specifically, the present invention relates to a compound having a structure having a bipyridyl group and carbazole ring, and an organic electroluminescent element using the compound.

BACKGROUND ART

An organic electroluminescent element is a self-light-emitting element and therefore, it is bright, is excellent in visibility, and enables clear display compared with a liquid crystal element, so that active researches have been made on it.

In recent years, as an attempt to increase light emission efficiency of elements, an element caused to emit phosphorescence by making use of a phosphorescent emitter, that is, using light emission from a triplet excited state has been developed. According to the theory on the excited state, using phosphorescence emission enables about 4 times greater emission efficiency than that caused by the conventional fluorescence emission and a marked improvement in emission efficiency can be expected.

In 1993, M. A. Baldo, et al. in Princeton University (US) realized an external quantum efficiency of 8% by making use of a phosphorescent element using an iridium complex.

A phosphorescent emitter causes concentration quenching so that it is supported by doped with a charge transporting compound generally called "host compound". The phosphorescent emitter to be supported is called a "guest compound". As the host compound, 4,4'-di(N-carbazolyl)biphenyl (hereinafter abbreviated as "CBP") represented by the following formula has ordinarily been used (for example, Non-Patent Document 1).

[Chem. 1]

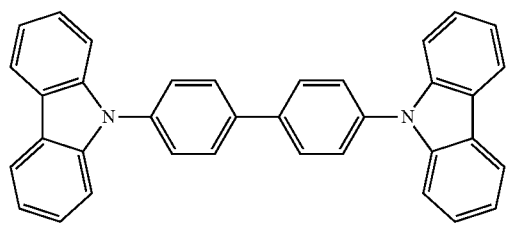

It has however been pointed out that CBP has a glass transition point (Tg) as low as 62° C. and has high crystallinity so that it has poor stability in a thin film state. As a result, in case where heat resistance is required, for example, in high-brightness light emission, satisfactory element properties had not been achieved.

With the progress of research on phosphorescent elements, an energy transfer process between a phosphorescent emitter and a host compound has been elucidated. It has therefore been revealed that in order to heighten an emission efficiency, the excited triplet level of the host compound should be higher than the excited triplet level of the phosphorescent emitter.

When a host compound of a light-emitting layer is obtained by doping FIrpic which is a blue phosphorescent material represented by the following formula with the CBP, the external quantum efficiency of the phosphorescent element remains at about 6%. This was presumed to occur due to insufficient confinement of triplet excitons with FIrpic because the excited triplet level of CBP is as low as 2.57 eV while the excited triplet level of FIrpic is 2.67 eV. This has been proved by that the photoluminescence intensity of a thin film obtained by doping CBP with FIrpic shows temperature dependence (Non-patent Document 2).

[Chem. 2]

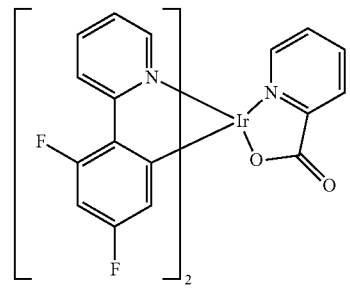

As a host compound having an excited triplet level higher than that of CBP, 1,3-bis(carbazol-9-yl)benzene (hereinafter abbreviated as "mCP") represented by the following formula has been known. This mCP has also a glass transition point (Tg) as low as 55° C. and has high crystallinity so that it has only poor stability in a thin film state. Therefore, in case where heat resistance is required, for example, in high-brightness light emission, satisfactory element properties had not been achieved (Non-patent Document 2).

[Chem. 3]

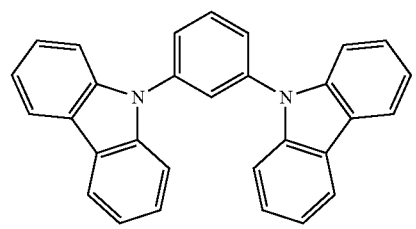

Further, as a result of investigation on host compounds having a higher excited triplet level, it has been found that when an iridium complex is doped with an electron-transporting or bipolar transporting host compound, high emission efficiency can be achieved (for example, Non-patent Document 3).

Thus, in order to enhance the emission efficiency of a phosphorescent element in practical utilization, there has been a demand for a host compound for a light-emitting layer, which has a high excited triplet level and high thin-film stability.

CITATION LIST

Patent Literature

Patent Document: JP-A-2007-022986

Non-Patent Literature

Non-patent Document 1: Appl. Phys. Let., 75, 4(1999)
Non-patent Document 2: Development and Evaluation Technology of Materials for Organic EL illumination, p 102-106, Science & Technology Co., Ltd. (2010)
Non-patent Document 3: Organic EL displays, p 90, Ohmsha (2005)
Non-patent Document 4: Synth. Commun., 11, 513(1981)
Non-patent Document 5: The fourth Series of Experimental Chemistry 7, p 384-398, ed. by The Chemical Society of Japan, pub. by Maruzen Publishing Co., Ltd. (1992)
Non-patent Document 6: Proceedings of the First Meeting, Conference on Organic EL, 19(2005)

SUMMARY OF THE INVENTION

Problem that the Invention is to Solve

An object of the present invention is to provide, as a material for high-efficiency organic electroluminescent element, a host compound of a light-emitting layer, which has a high excited triplet level, is capable of completely confining a triplet exciton of a phosphorescent emitter, and at the same time has high thin-film stability, in other words, has a high glass transition point (Tg); and to provide a high-efficiency and high-brightness organic electroluminescent element by using the compound. The organic compound to be provided by the present invention is required to have the following physical properties: (1) having a high excited triplet level, (2) having a bipolar transporting property, and (3) having stability in a thin film state. The organic electroluminescent element to be provided by the present invention is required to have the following physical characteristics: (1) having a high emission efficiency, (2) having a high emission brightness, and (3) having a low practical driving voltage.

Means for Solving the Problem

With a view to achieving the above objects, the present inventors designed and chemically synthesized compounds with an excited triplet level as an indicator while paying attention to a bipyridyl structure having an electron-transporting ability and a carbazole structure having a hole-transporting ability. By measuring the excited triplet level in practice, they have found novel compound having a bipyridyl group and carbazole ring, which has properties suited for use in a phosphorescent emitter. Then, they produced various organic electroluminescent elements by way of trial by using the compounds, and as a result of intensive evaluation of the properties of these elements, they have completed the present invention.

That is, the present invention provides a compound having a bipyridyl group and a carbazole ring, which is represented by the following general formula (1).

[Chem. 4]

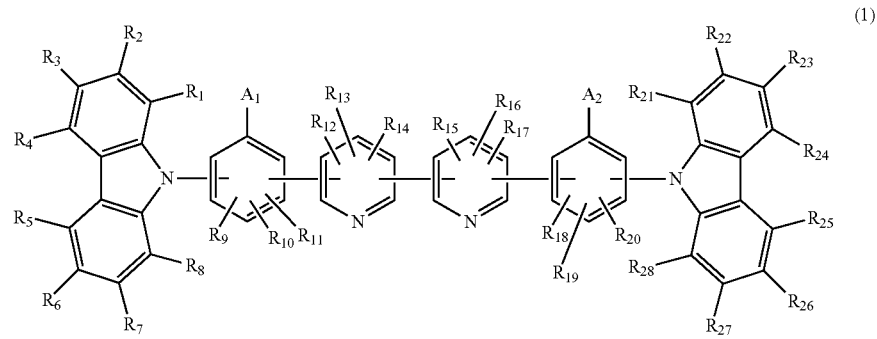

(1)

(In the formula, $A_1$ and $A_2$ may be the same or different and represent a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group; and $R_1$ to $R_{28}$ may be the same or different and represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.)

The compound having a bipyridyl group and a carbazole ring is preferably a compound having a bipyridyl group and a carbazole ring, which is represented by the following general formula (2).

[Chem. 5]

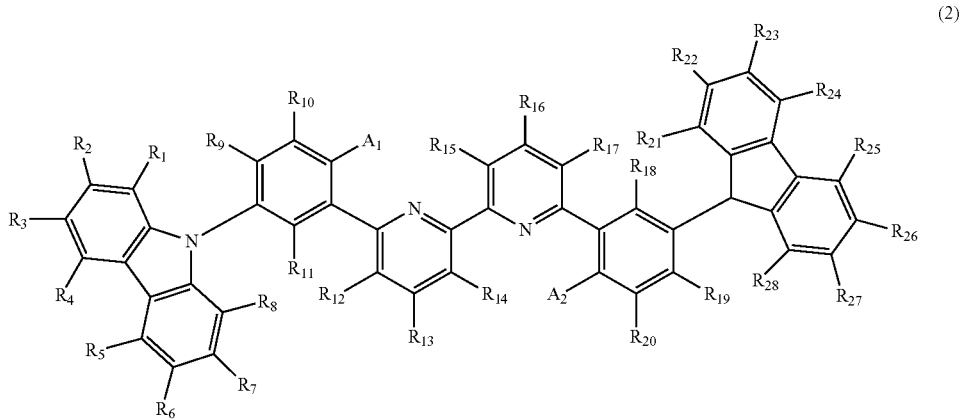

(2)

(In the formula, $A_1$ and $A_2$ may be the same or different and represent a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group; and $R_1$ to $R_{28}$ may be the same or different and represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.)

Also, the compound having a bipyridyl group and a carbazole ring is preferably a compound having a bipyridyl group and a carbazole ring, which is represented by the following general formula (3).

[Chem. 6]

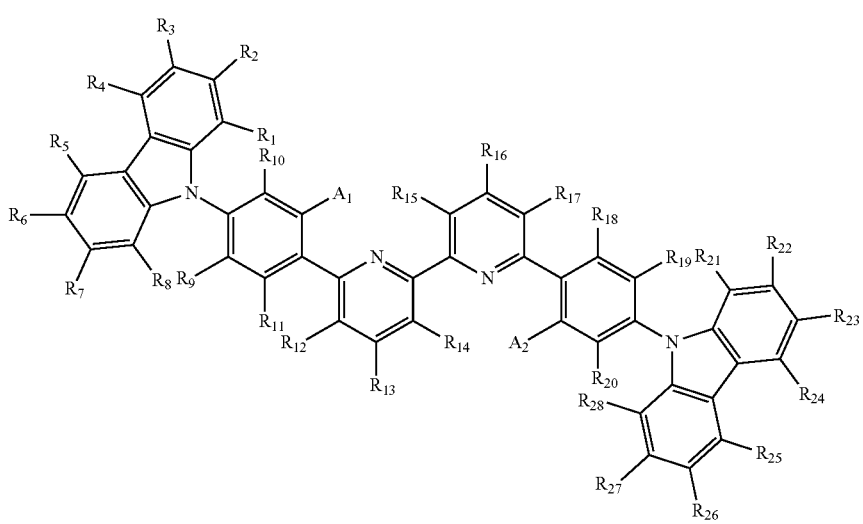

(3)

(In the formula, $A_1$ and $A_2$ may be the same or different and represent a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group; and $R_1$ to $R_{28}$ may be the same or different and represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.)

Further, the present invention provides an organic electroluminescent element comprising a pair of electrodes and at least one organic layer interposed therebetween, in which the compound represented by the general formula (1) is contained in the at least one organic layer as a constituent material thereof In the organic electroluminescent element according to the present invention, it is preferred that the organic layer is a light-emitting layer and the compound represented by the general formula (1) is contained in the light-emitting layer as a constituent material thereof.

Further, the organic electroluminescent element according to the present invention is preferably an organic electroluminescent element comprising a pair of electrodes, and a light-emitting layer containing a phosphorescent light-emitting material and at least one organic layer which are interposed therebetween, in which the compound represented by the general formula (1) is contained in the light-emitting layer as a constituent material thereof.

Further, the organic electroluminescent element according to the present invention is preferably an organic electroluminescent element comprising a pair of electrodes, and a light-emitting layer containing a phosphorescent light-emitting material and at least one organic layer which are interposed therebetween, in which the compound represented by the general formula (1) is contained in the at least one organic layer as a constituent material thereof.

Further, in the organic electroluminescent element according to the present invention, it is preferred that the organic layer is a hole-blocking layer and the compound represented by the general formula (1) is contained in the hole-blocking layer as a constituent material thereof.

Further, in the organic electroluminescent element according to the present invention, it is preferred that the phosphorescent light-emitting material is a metal complex containing iridium or platinum.

Specific examples of the "aromatic hydrocarbon group", "aromatic heterocyclic group" or "condensed polycyclic aromatic group" of the "substituted or unsubstituted aromatic hydrocarbon group", "substituted or unsubstituted aromatic heterocyclic group" or "substituted or unsubstituted condensed polycyclic aromatic group", each represented by $R_1$ to $R_{28}$ in the general formula (1) include a phenyl group, a biphenylyl group, a terphenylyl group, a tetrakisphenyl group, a styryl group, a naphthyl group, an anthryl group, an acenaphthenyl group, a phenanthryl group, a fluorenyl group, an indenyl group, a pyrenyl group, a pyridyl group, a triazyl group, a pyrimidyl group, a furanyl group, a pyronyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group, and an acridinyl group.

Specific examples of the "substituent" in the "substituted aromatic hydrocarbon group", "substituted aromatic heterocyclic group" or "substituted condensed polycyclic aromatic group", each represented by $R_1$ to $R_{28}$ in the general formula (1) include a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a phenyl group, a biphenylyl group, a terphenylyl group, a naphthyl group, a phenanthryl group, an aralkyl group, a fluorenyl group, an indenyl group, a pyridyl group, a pyrimidyl group, a furanyl group, a pyronyl group, a thienyl group, a quinolyl group, a benzofuranyl group, a benzothienyl group, an indolyl group, a carbazolyl group, a carboryl group, a benzoxazolyl group, a quinoxalyl group, a benzimidazolyl group, a pyrazolyl group, a dibenzofuranyl group, and a dibenzothienyl group. These substituents may be substituted further.

Specific examples of the "linear or branched alkyl group having from 1 to 6 carbon atoms" or "linear or branched alkoxy group having from 1 to 6 carbon atoms", each represented by $R_1$ to $R_{28}$ in the general formula (1), include a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, a t-hexyl group, a methoxy group, an ethoxy group, an n-propyloxy group, an i-propyloxy group, an n-butyloxy group, an i-butyloxy group, a t-butyloxy group, an n-pentyloxy group, an i-pentyloxy group, a t-pentyloxy group, an n-hexyloxy group, an i-hexyloxy group, and a t-hexyloxy group.

Specific examples of the "aromatic hydrocarbon group", "aromatic heterocyclic group" or "condensed polycyclic aromatic group" of the "substituted or unsubstituted aromatic hydrocarbon group", "substituted or unsubstituted aromatic heterocyclic group" or "substituted or unsubstituted condensed polycyclic aromatic group", each represented by $A_1$ or $A_2$ in the general formula (1) include a phenyl group, a biphenylyl group, a terphenylyl group, a tetrakisphenyl group, a styryl group, a naphthyl group, an anthryl group, an acenaphthenyl group, a phenanthryl group, a fluorenyl group, an indenyl group, a pyrenyl group, a pyridyl group, a triazyl group, a pyrimidyl group, a furanyl group, a pyronyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group, and an acridinyl group.

Specific examples of the "substituent" in the "substituted or unsubstituted aromatic hydrocarbon group", "substituted or unsubstituted aromatic heterocyclic group" or "substituted or unsubstituted condensed polycyclic aromatic group", each represented by $A_1$ or $A_2$ in the general formula (1) include a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a phenyl group, a biphenylyl group, a terphenylyl group, a naphthyl group, a phenanthryl group, an aralkyl group, a fluorenyl group, an indenyl group, a pyridyl group, a pyrimidyl group, a furanyl group, a pyronyl group, a thienyl group, a quinolyl group, a benzofuranyl group, a benzothienyl group, an indolyl group, a carbazolyl group, a carboryl group, a benzoxazolyl group, a quinoxalyl group, a benzimidazolyl group, a pyrazolyl group, a dibenzofuranyl group, and a dibenzothienyl group. These substituents may be substituted further.

Specific examples of the "linear or branched alkyl group having from 1 to 6 carbon atoms" or "linear or branched alkoxy group having from 1 to 6 carbon atoms", each represented by $A_1$ or $A_2$ in the general formula (1) include a methyl group, an ethyl group, an n-propyl group, an i-propyl group, an n-butyl group, an i-butyl group, a t-butyl group, an n-pentyl group, an i-pentyl group, a t-pentyl group, an n-hexyl group, an i-hexyl group, a t-hexyl group, a methoxy group, an ethoxy group, an n-propyloxy group, an i-propyloxy group, an n-butyloxy group, an i-butyloxy group, a t-butyloxy group, an n-pentyloxy group, an i-pentyloxy group, a t-pentyloxy group, an n-hexyloxy group, an i-hexyloxy group, and a t-hexyloxy group.

The compound having a bipyridyl group and carbazole ring, represented by the general formula (1) according to the present invention is a novel compound, has an excited triplet level higher than that of conventional materials for a hole-blocking layer, has an excellent ability of confining triplet excitons, and has stability in a thin film state.

The compound having a bipyridyl group and carbazole ring, represented by the general formula (1) according to the present invention can be used as a constituent material for a light-emitting layer or hole-blocking layer of an organic electroluminescent element (hereinafter abbreviated as "organic EL element"). By using the compound of the present invention superior in bipolar transport property to conventional materials, there can be achieved effects that power efficiency is improved and practical driving voltage is decreased.

Advantageous Effect of the Invention

The compound having a bipyridyl group and carbazole ring of the present invention is useful as a hole-blocking compound or a host compound of a light-emitting layer to be used in an organic EL element. When an organic EL element is fabricated using the compound, an organic EL element having high efficiency, high brightness, and low driving voltage can be obtained.

MODE FOR CARRYING OUT THE INVENTION

Figure 1:
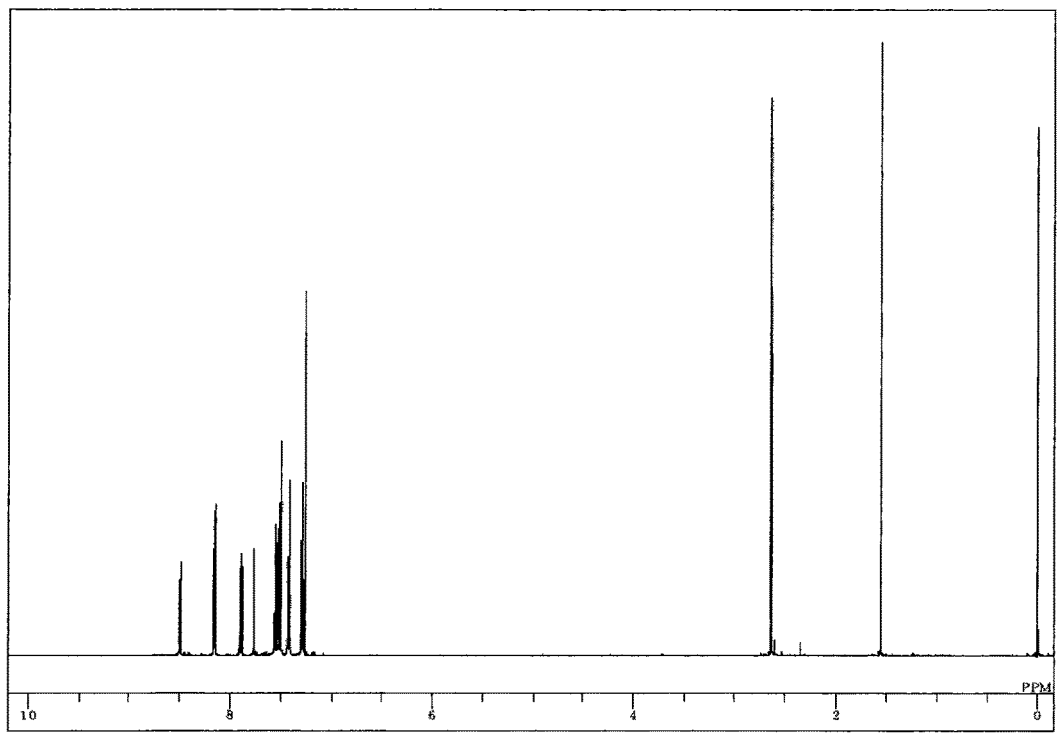
FIG. 1 is a $^1$H-NMR chart of the compound of Example 1 of the present invention (Compound 13).

The compounds having a bipyridyl group and carbazole ring according to the present invention are novel compounds and these compounds can be synthesized, for example, as follows. First, a corresponding carbazolylphenyl intermediate can be synthesized by carrying out a condensation reaction such as Ullmann reaction or Buchward-Hartwig reaction between a corresponding carbazole derivative and a corresponding dihalogenated benzene derivative. After synthesizing a corresponding boric acid ester from the corresponding carbazolylphenyl intermediate, a cross coupling reaction (refer to, for example, Non-patent Document 4) such as Suzuki coupling with a corresponding dihalogenated bipyridyl derivative is conducted, to thereby synthesize the compound having a bipyridyl group and carbazole ring of the present invention. The compound having a bipyridyl group and carbazole ring of the present invention can also be synthesized by carrying out, after synthesizing a corresponding bisboric acid ester synthesized from the dihalogenated bipyridyl derivative, a cross-coupling reaction (refer to, for example, Non-patent Document 4) such as Suzuki coupling with the corresponding carbazolylphenyl intermediate.

Among the compounds having a bipyridyl group and carbazole ring, represented by the general formula (1), following are specific examples of preferred compounds. The present invention is however not limited to these compounds.

[Chem. 7]

(Compound 4)

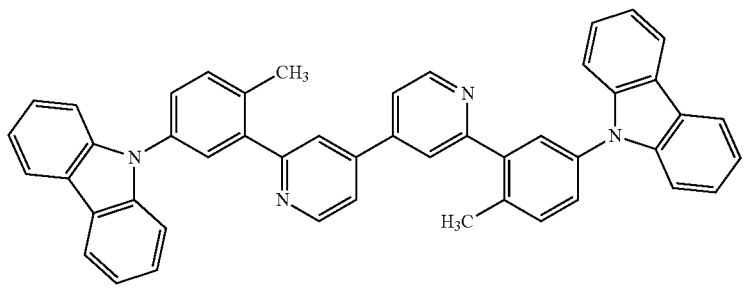

[Chem. 8]

(Compound 5)

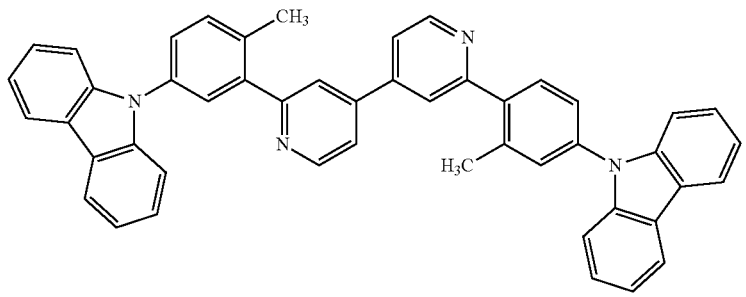

-continued
[Chem. 9]
(Compound 6)
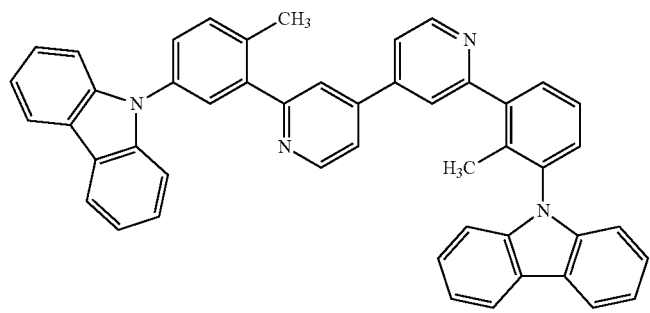
[Chem. 10]
(Compound 7)
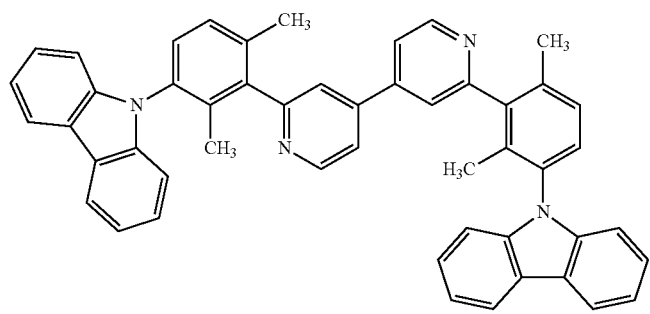
[Chem. 11]
(Compound 8)
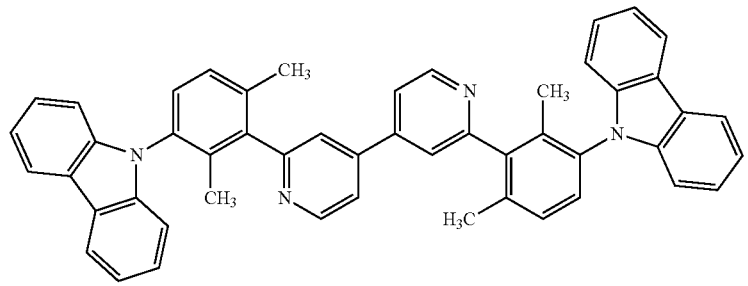
[Chem. 12]
(Compound 9)
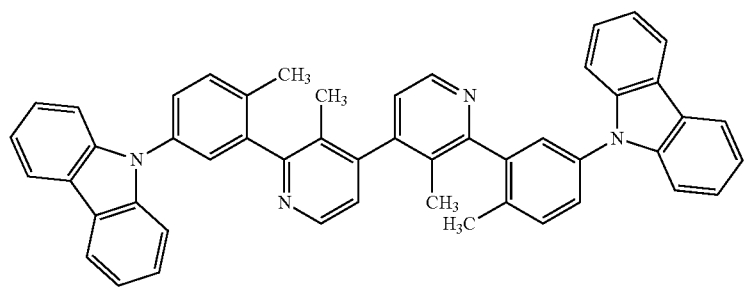

-continued
[Chem. 13]
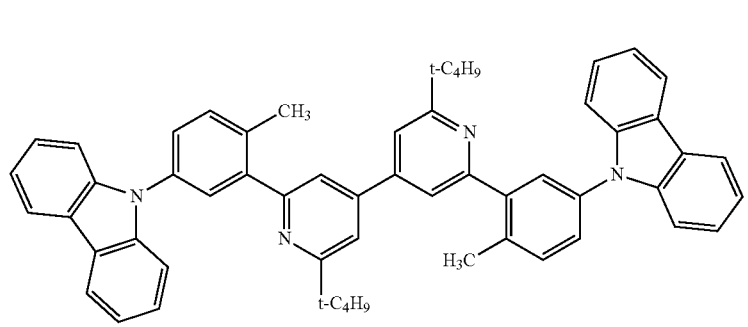
(Compound 10)
[Chem. 14]
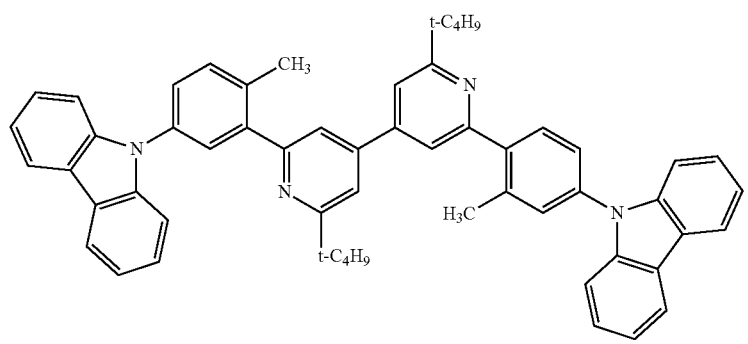
(Compound 11)
[Chem. 15]
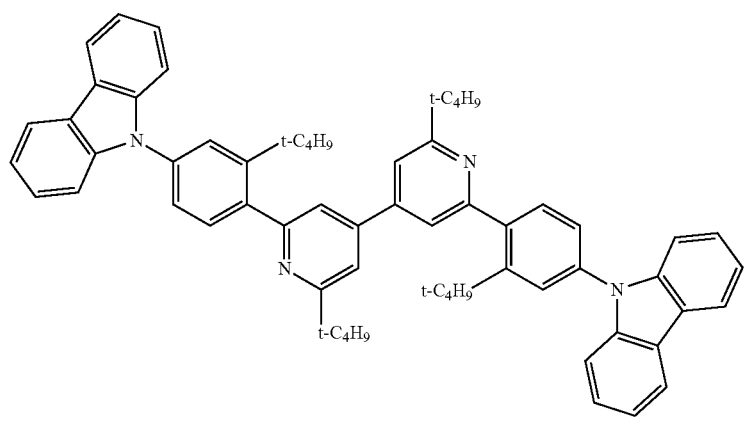
(Compound 12)
[Chem. 16]
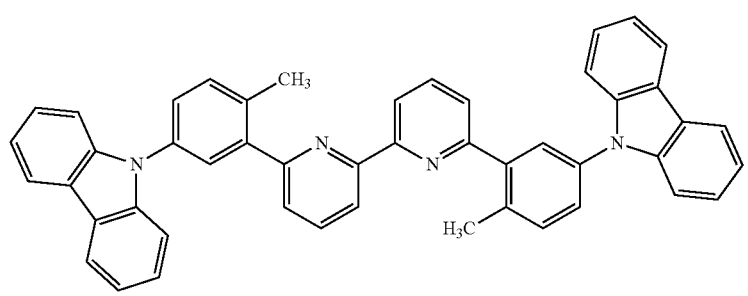
(Compound 13)

-continued
[Chem. 17]
(Compound 14)
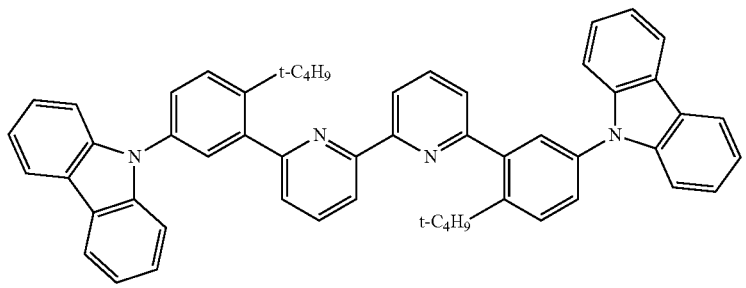
[Chem. 18]
(Compound 15)
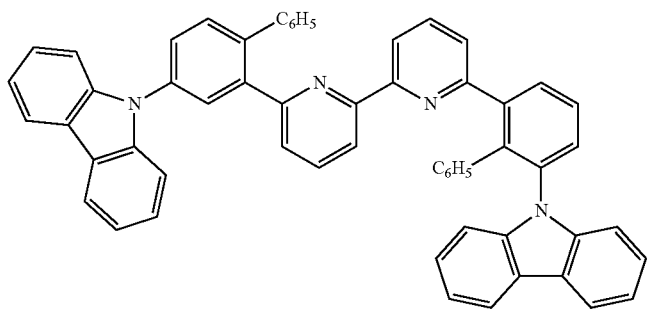
[Chem. 19]
(Compound 16)
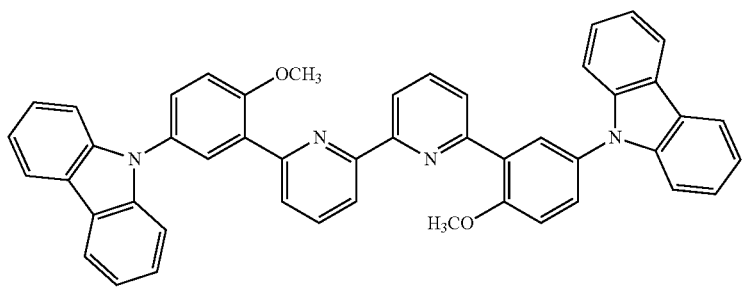
[Chem. 20]
(Compound 17)
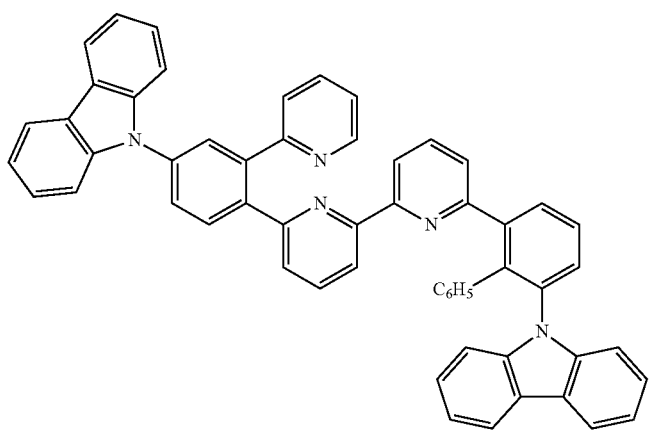

-continued
[Chem. 21]
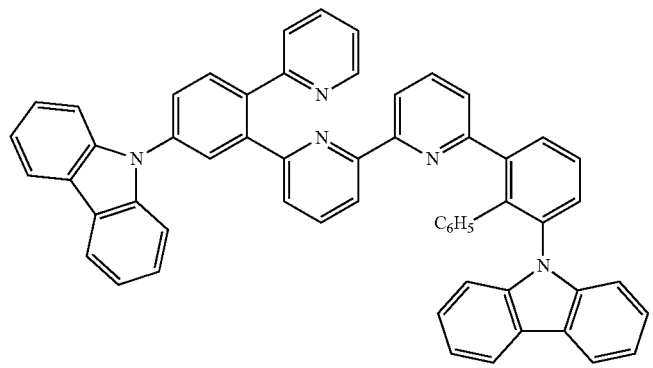
(Compound 18)
[Chem. 22]
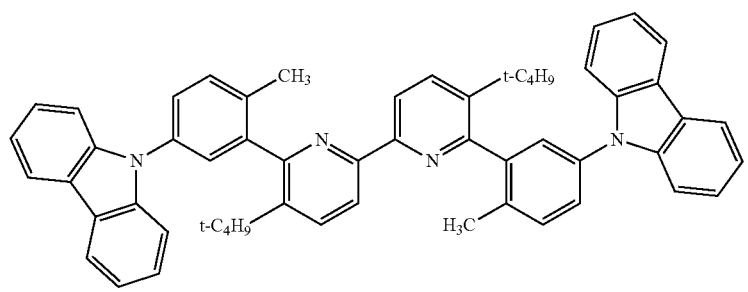
(Compound 19)
[Chem. 23]
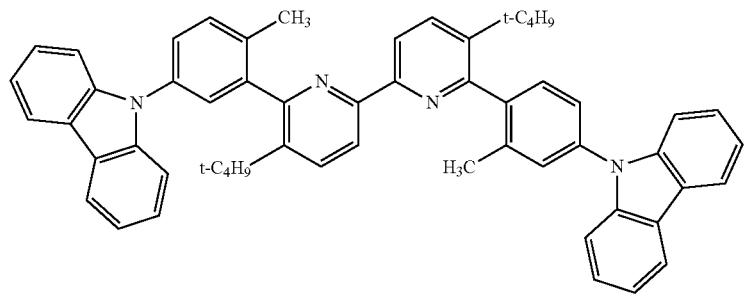
(Compound 20)
[Chem. 24]
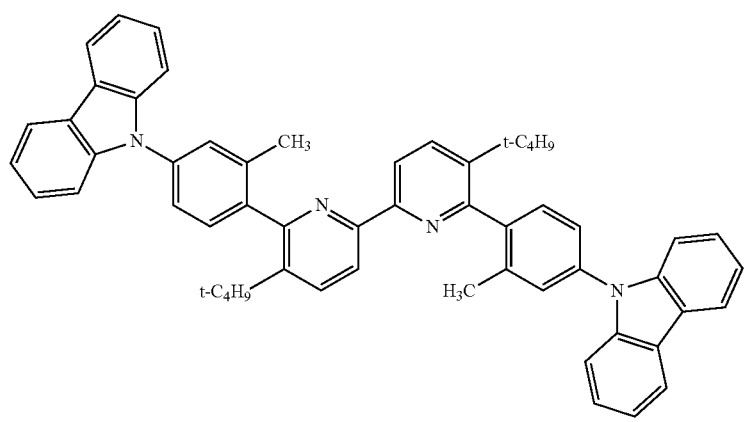
(Compound 21)

-continued
[Chem. 25]
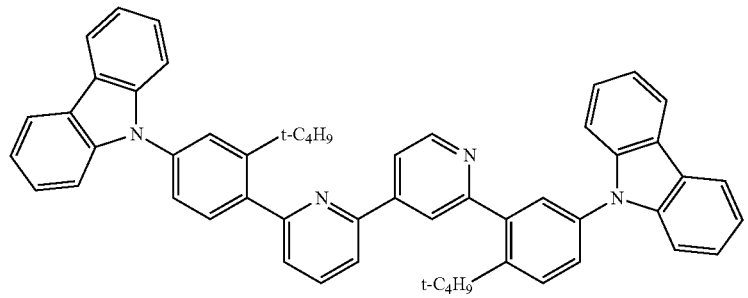
(Compound 22)
[Chem. 26]
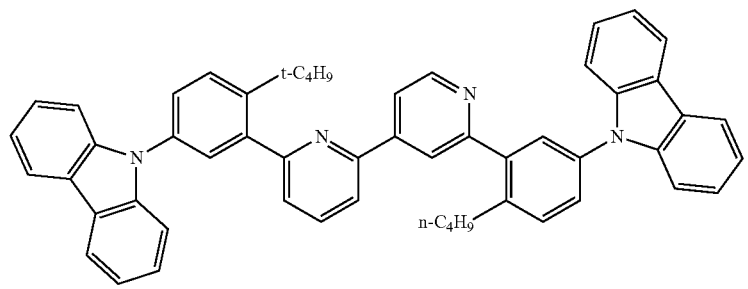
(Compound 23)
[Chem. 27]
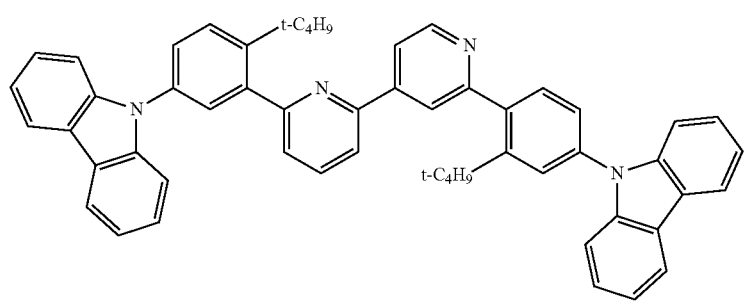
(Compound 24)
[Chem. 28]
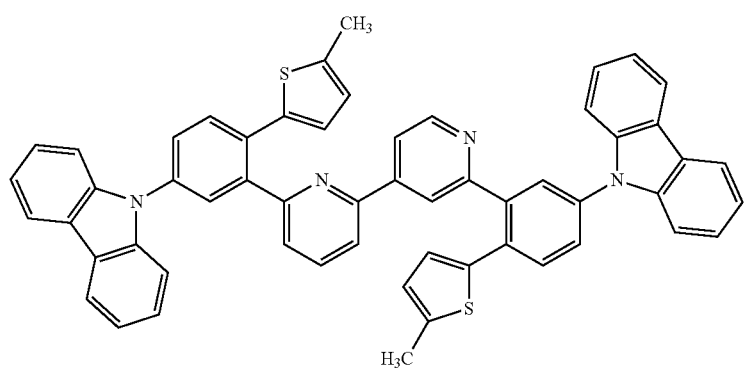
(Compound 25)

-continued
[Chem. 29]
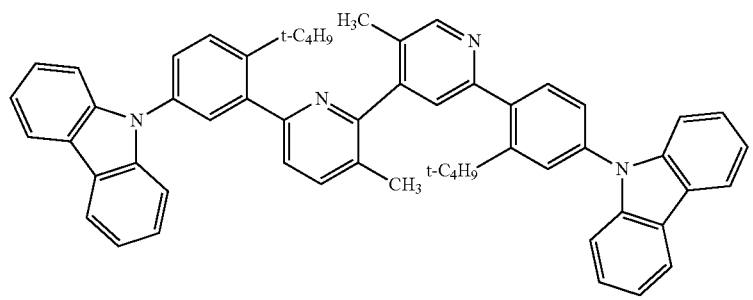
(Compound 26)
[Chem. 30]
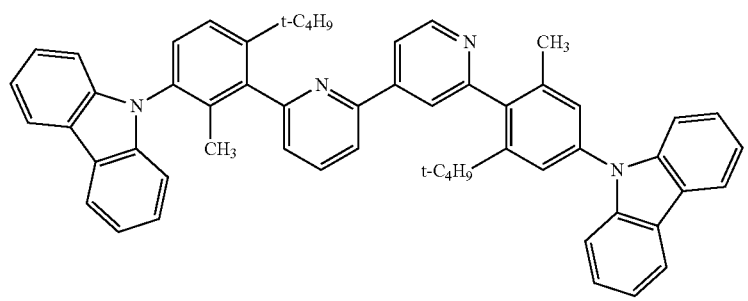
(Compound 27)
[Chem. 31]
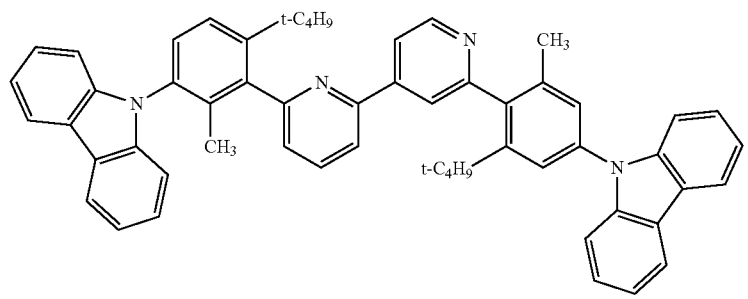
(Compound 28)
[Chem. 32]
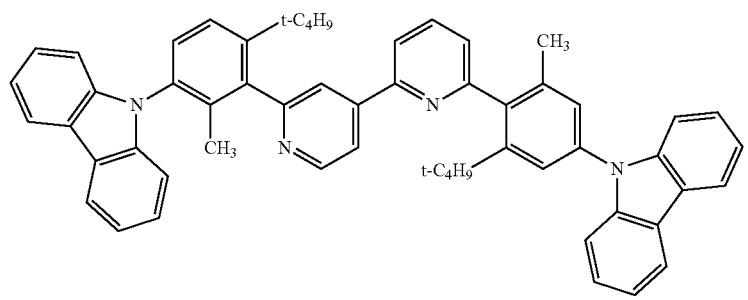
(Compound 29)

-continued
[Chem. 33]
(Compound 30)
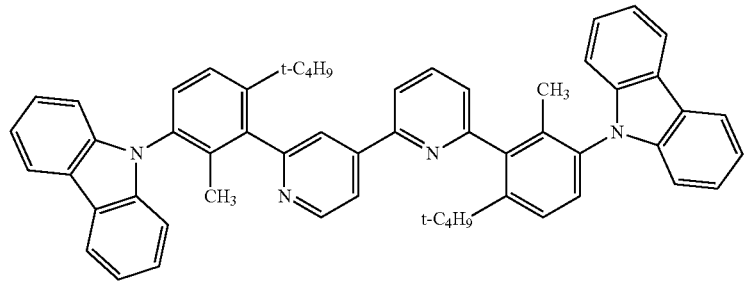
[Chem. 34]
(Compound 31)
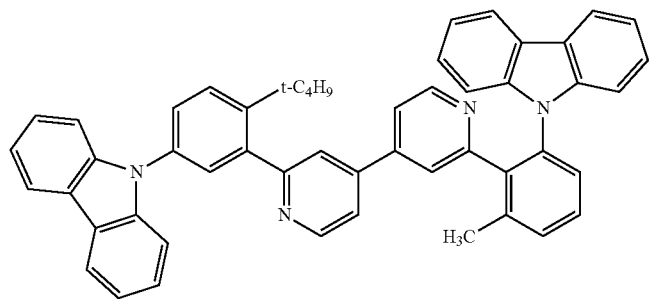
[Chem. 35]
(Compound 32)
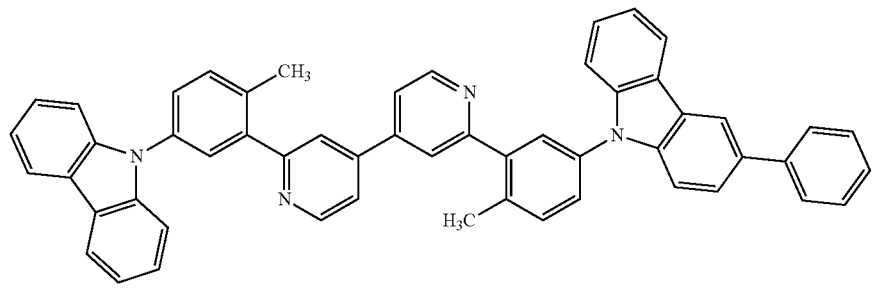
[Chem. 36]
(Compound 33)
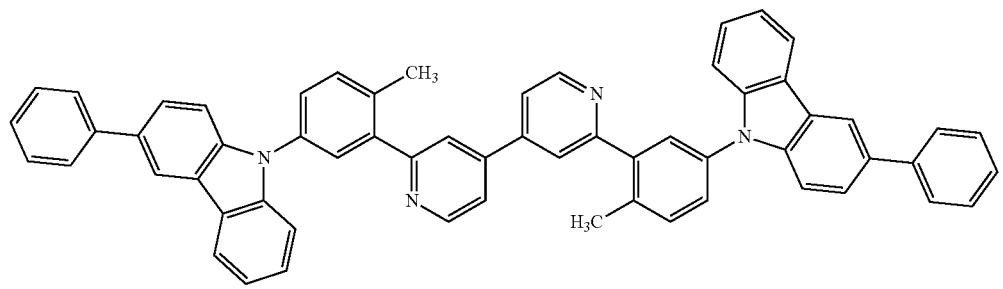

[Chem. 37]
(Compound 34)
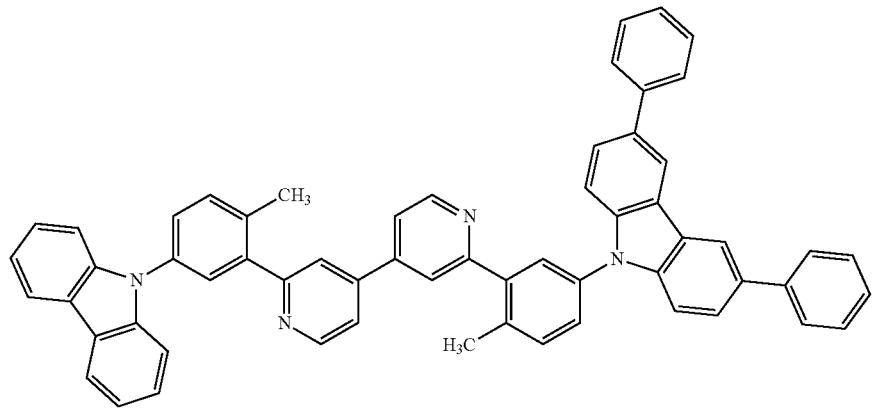
[Chem. 38]
(Compound 35)
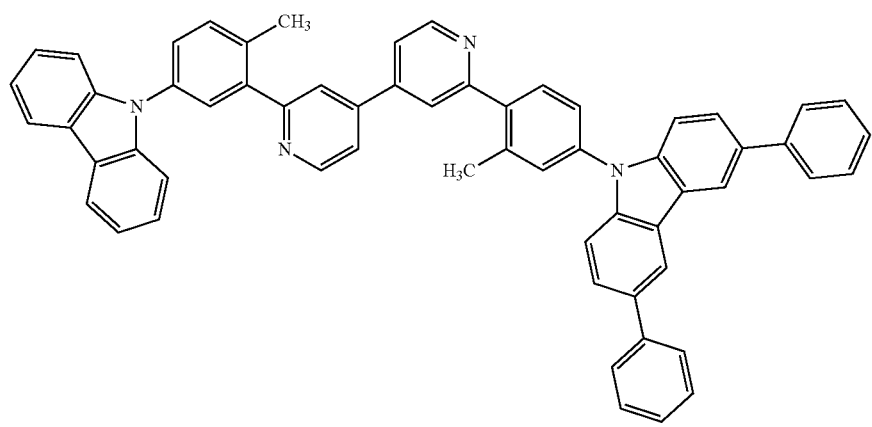
[Chem. 39]
(Compound 36)
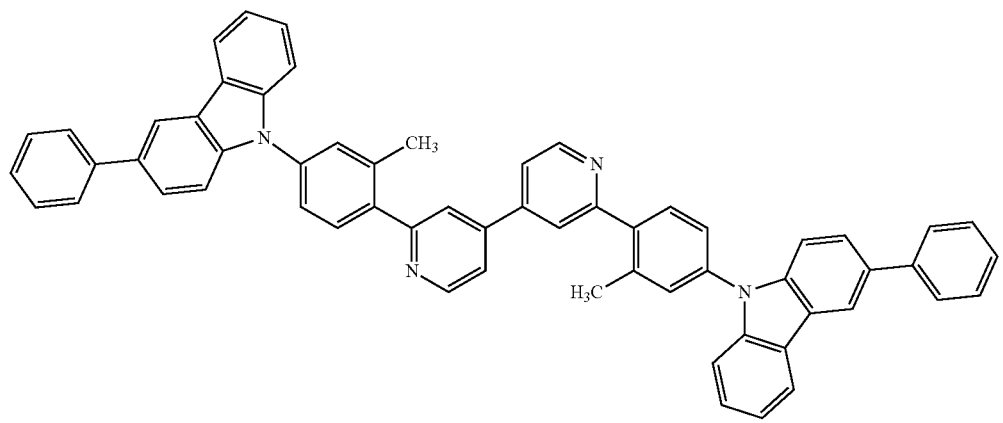

-continued
[Chem. 40]
(Compound 37)
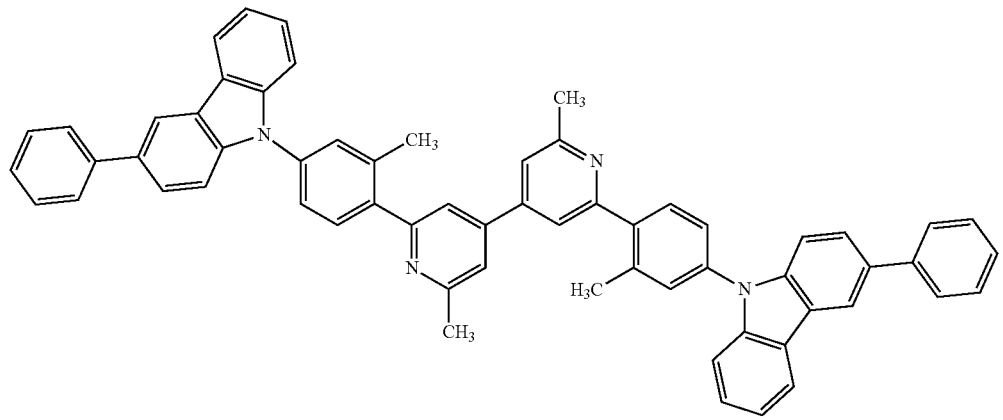
[Chem. 41]
(Compound 38)
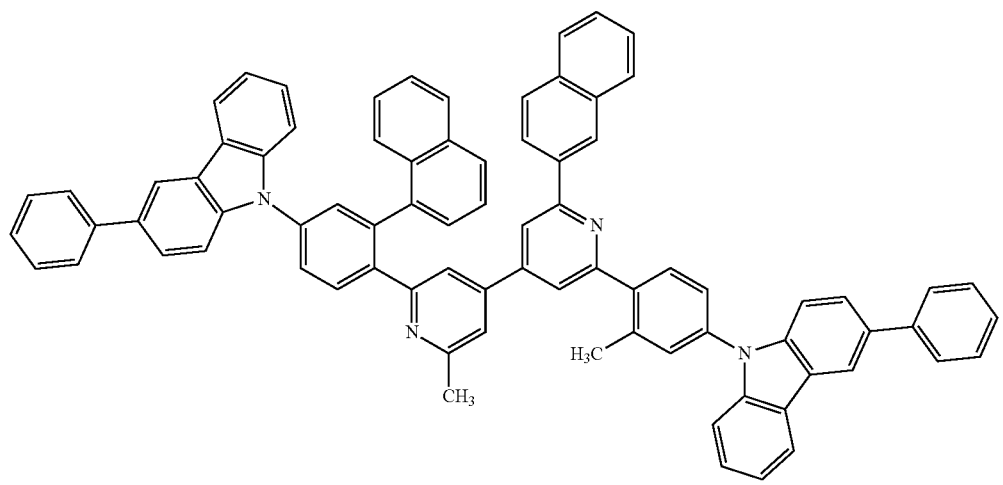
[Chem. 42]
(Compound 39)
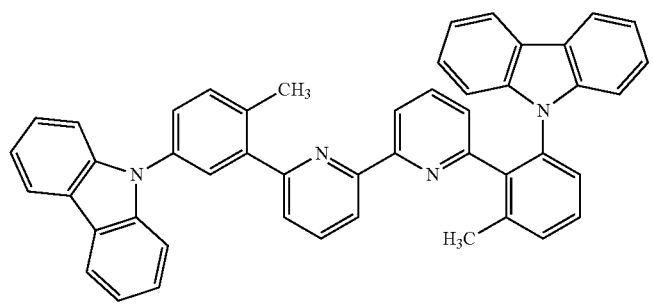

[Chem. 43]
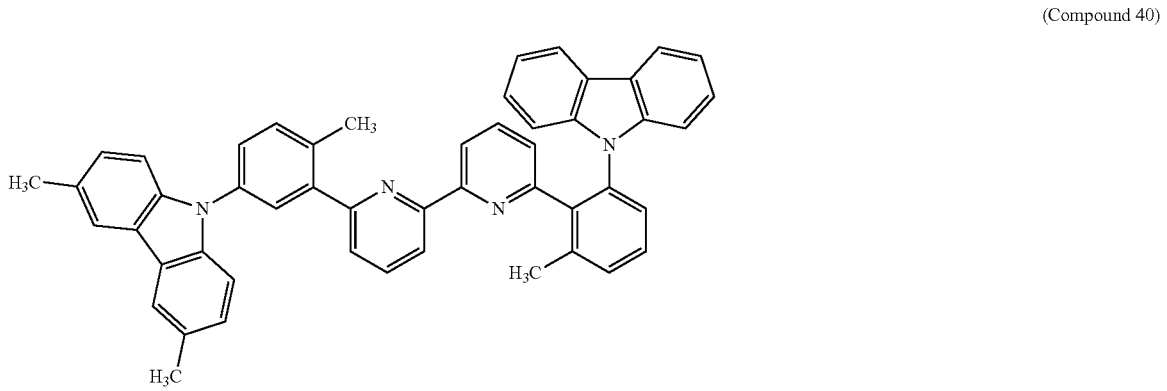
(Compound 40)
[Chem. 44]
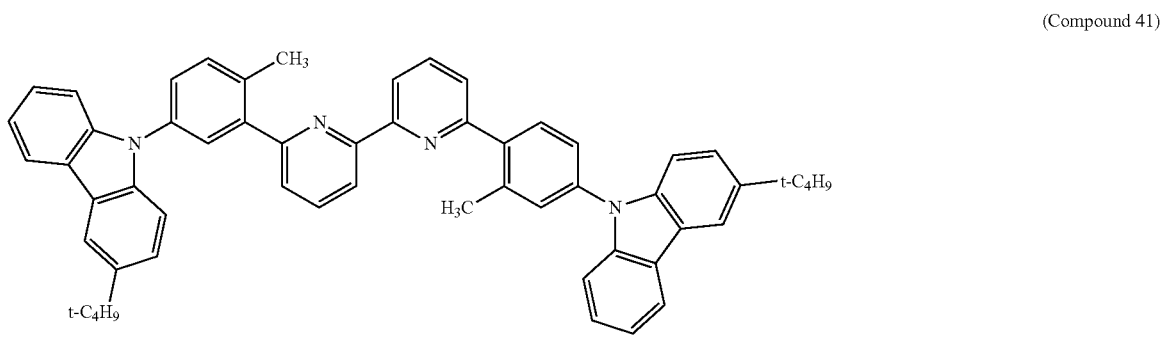
(Compound 41)
[Chem. 45]
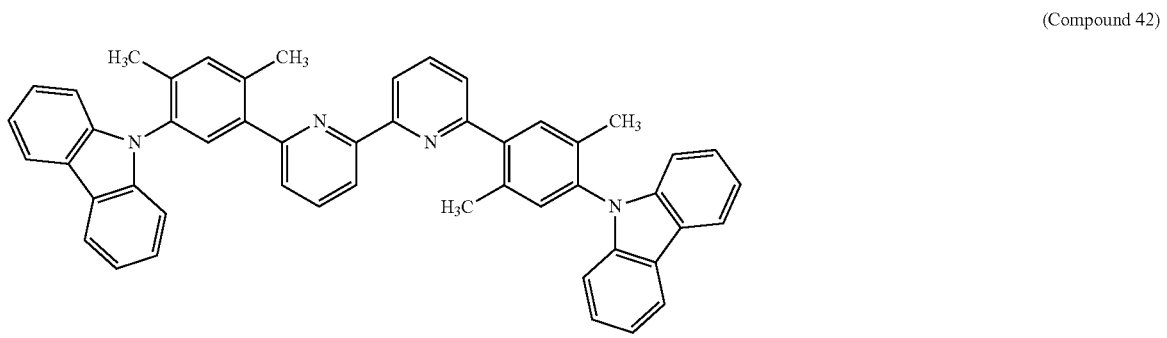
(Compound 42)
[Chem. 46]
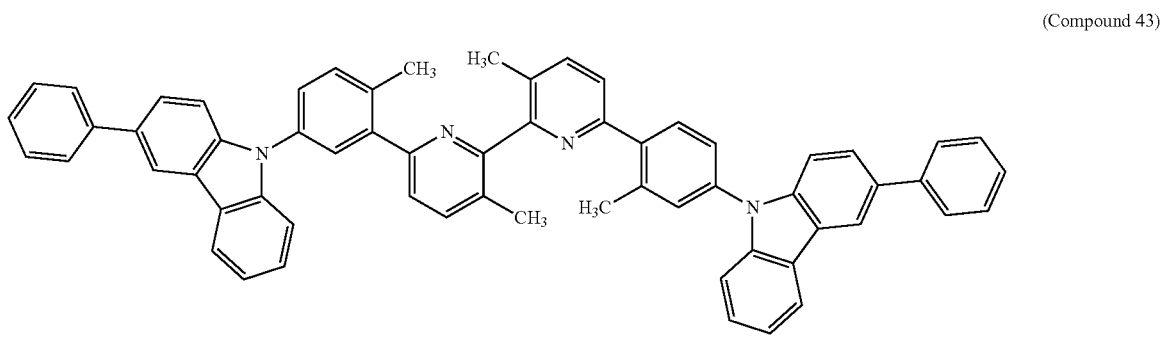
(Compound 43)

-continued
[Chem. 47]
(Compound 44)
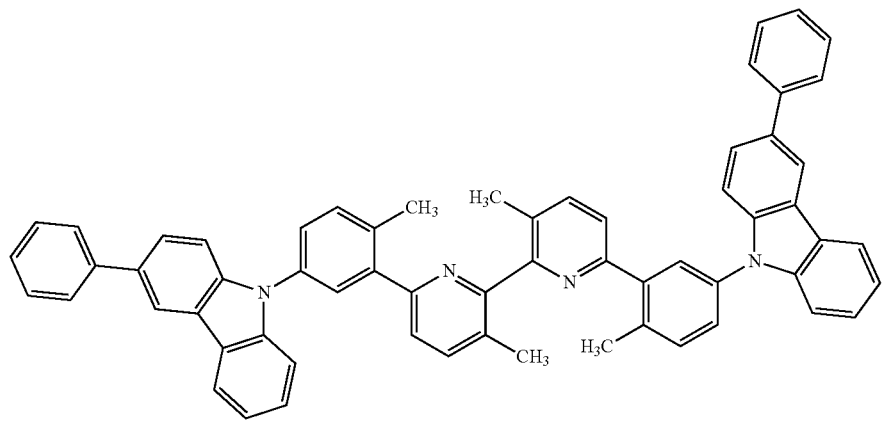
[Chem. 48]
(Compound 45)
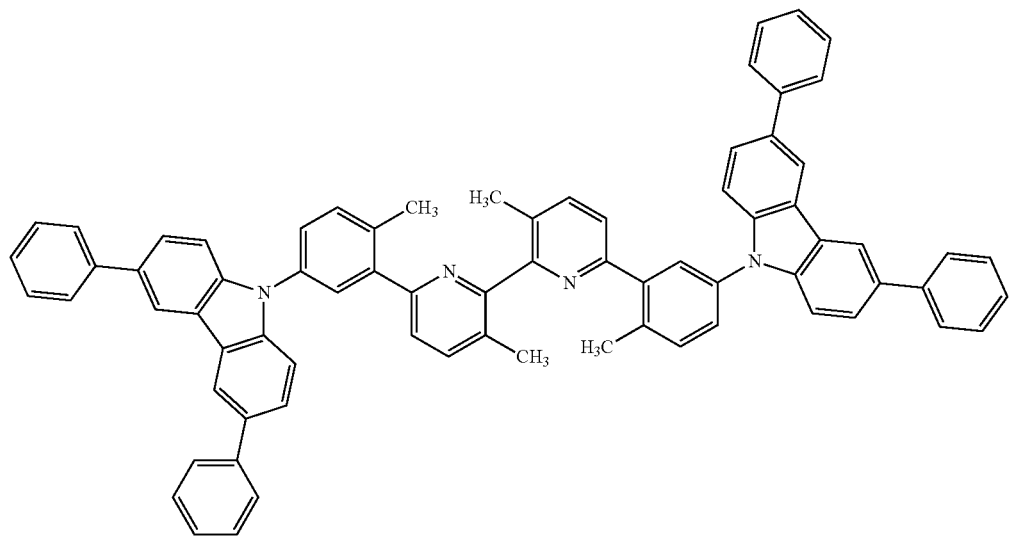
[Chem. 49]
(Compound 46)
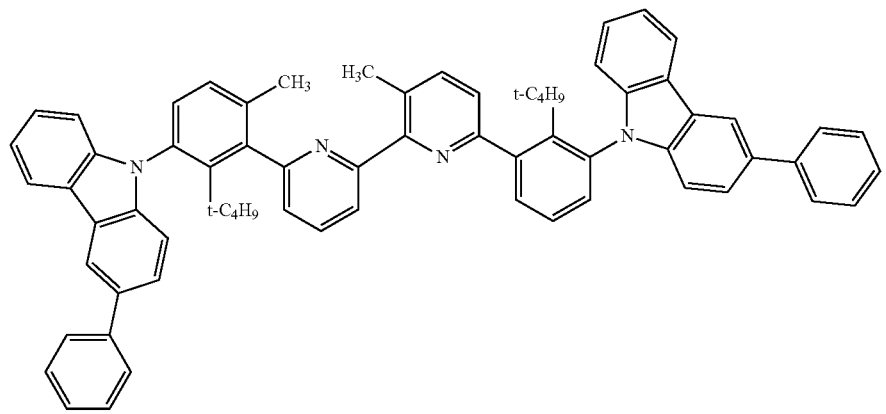

[Chem. 50]
(Compound 47)
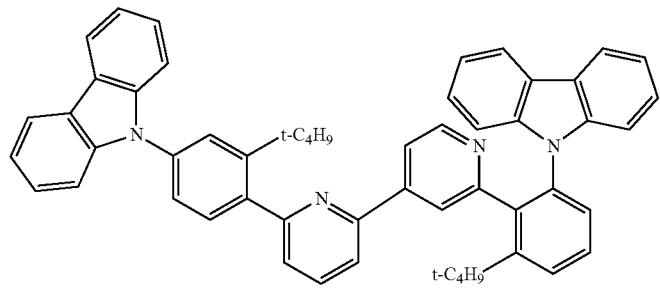
[Chem. 51]
(Compound 48)
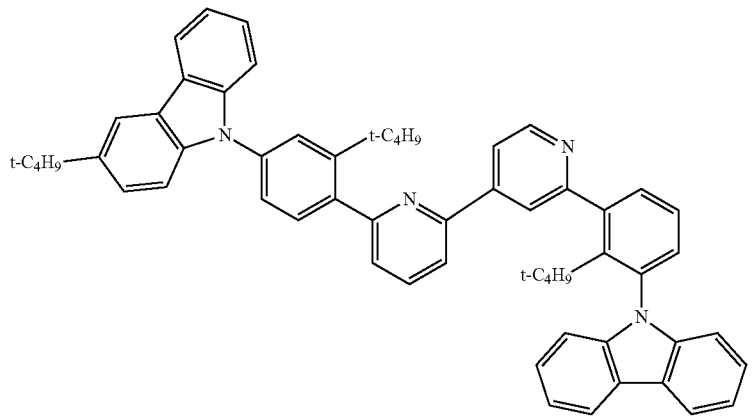
[Chem. 52]
(Compound 49)
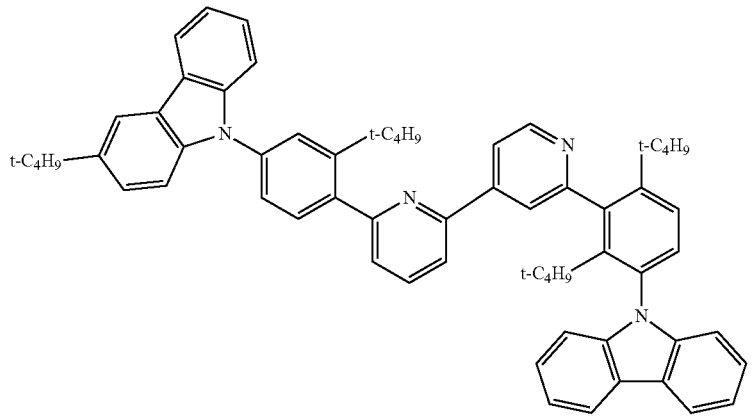

-continued
(Compound 50)
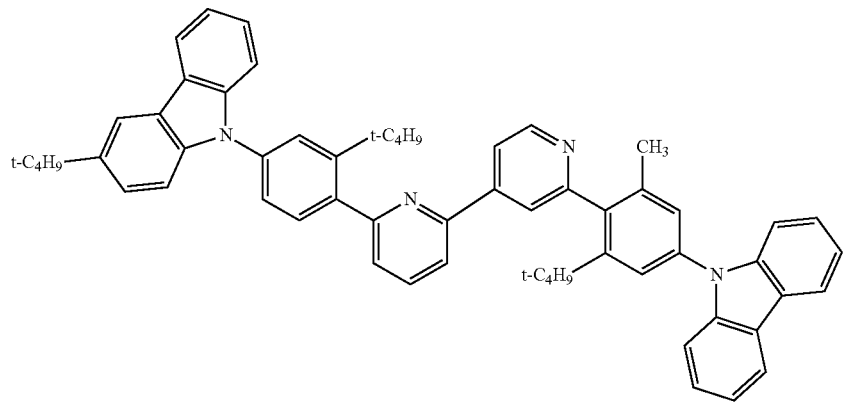
(Compound 51)
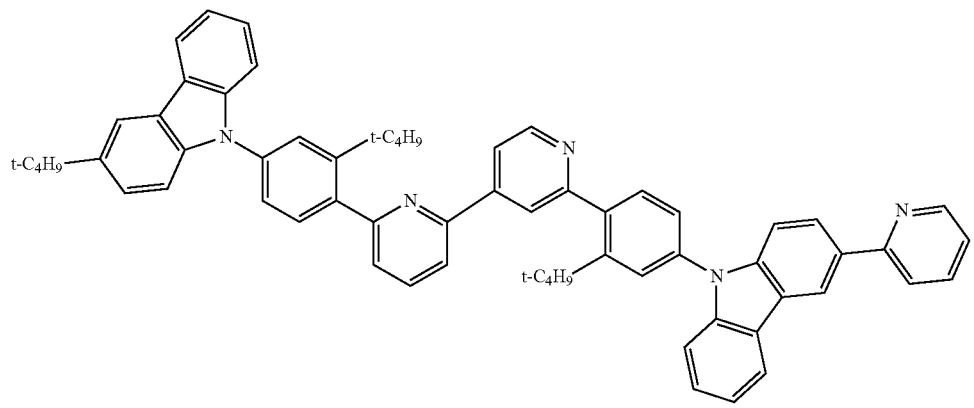
(Compound 52)
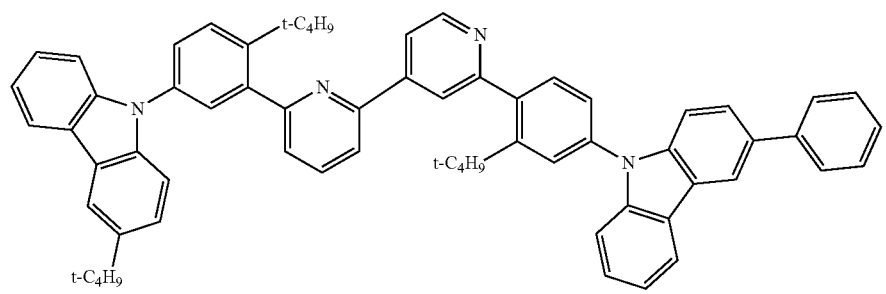
(Compound 53)
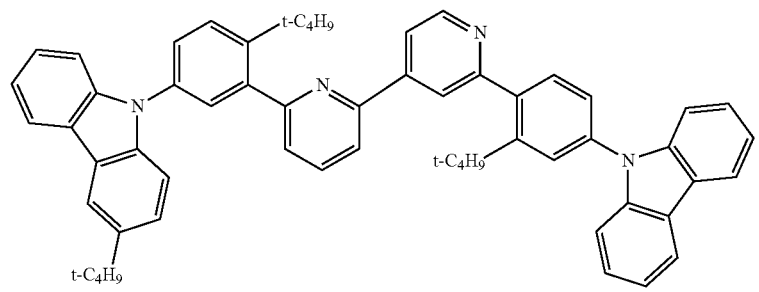

-continued
[Chem. 57]
(Compound 54)
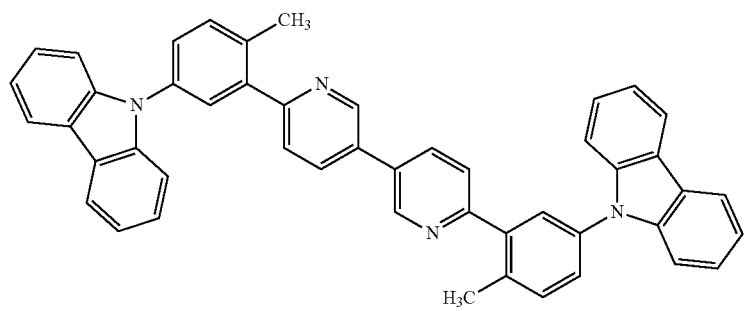
[Chem. 58]
(Compound 55)
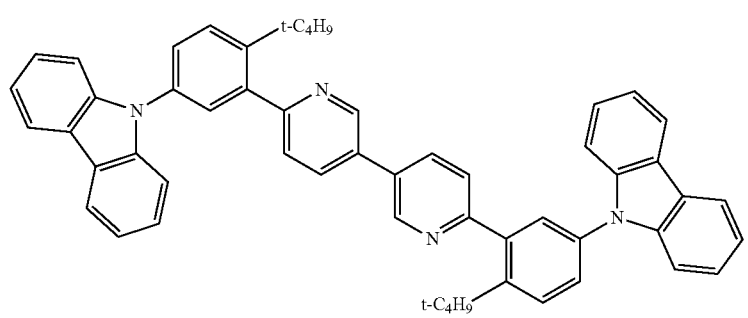
[Chem. 59]
(Compound 56)
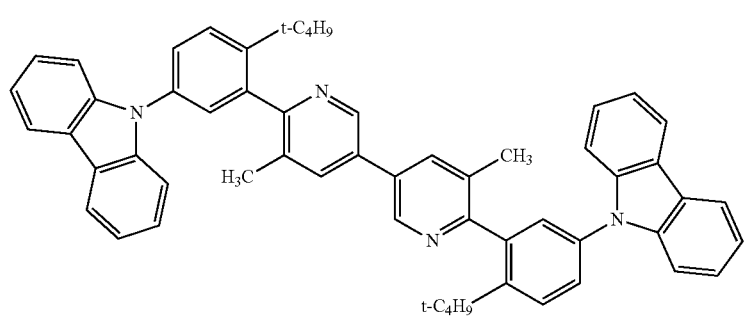
[Chem. 60]
(Compound 57)
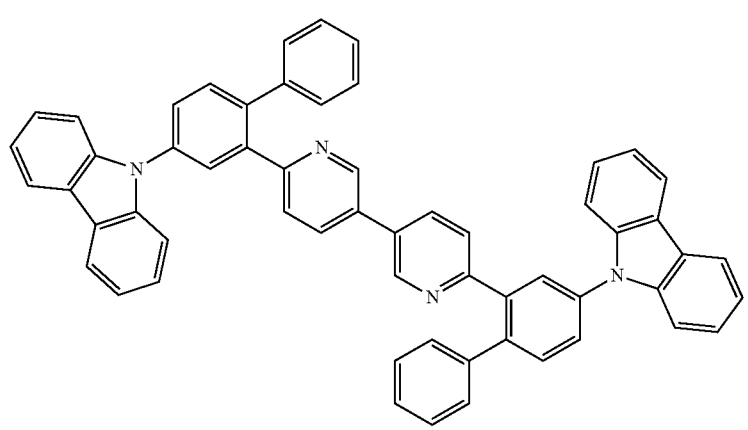

[Chem. 61]
(Compound 58)
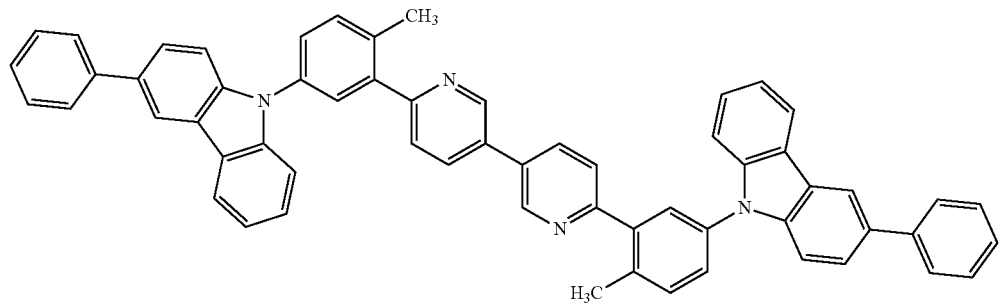
[Chem. 62]
(Compound 59)
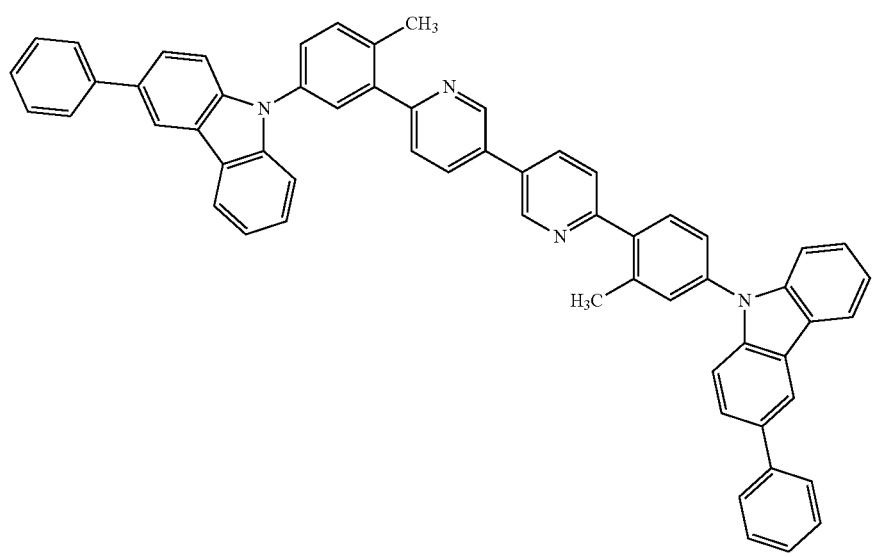
[Chem. 63]
(Compound 60)
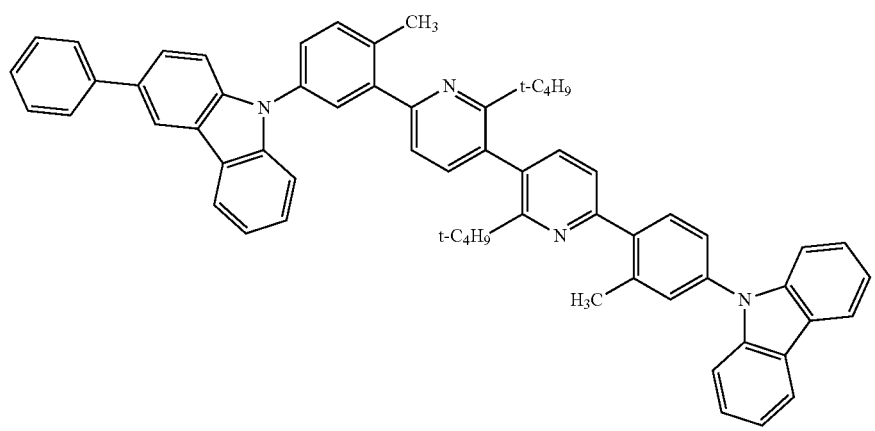

-continued
[Chem. 64]
(Compound 61)
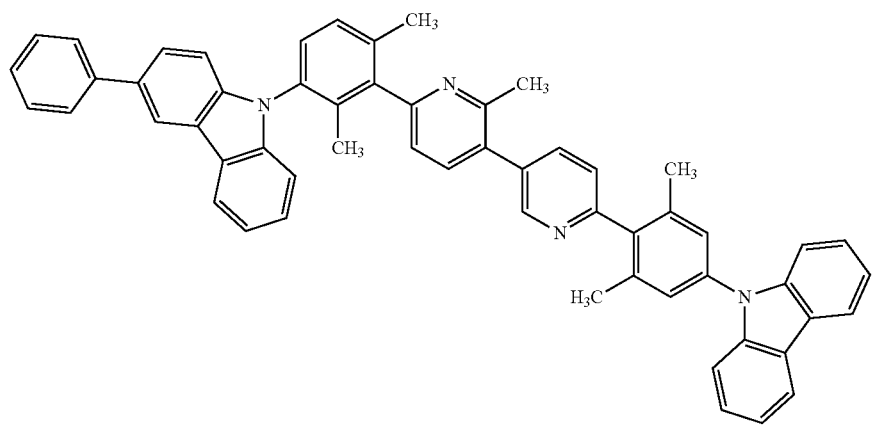
[Chem. 65]
(Compound 62)
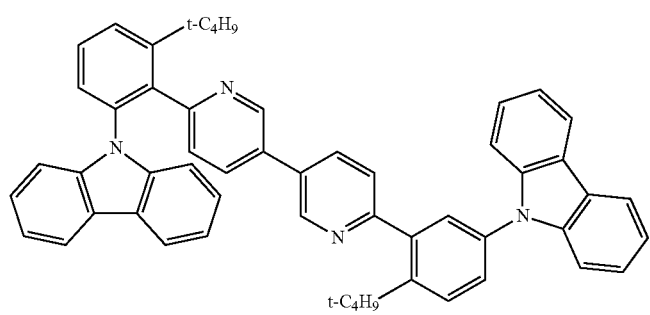
[Chem. 66]
(Compound 63)
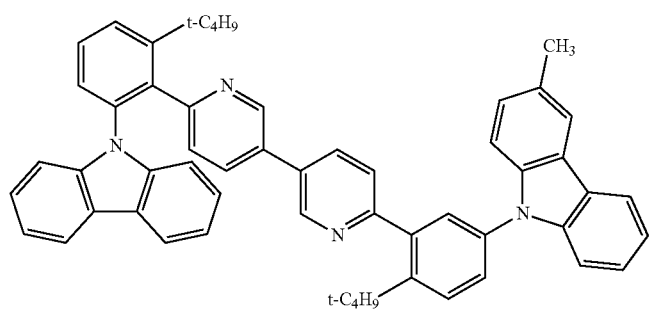
[Chem. 67]
(Compound 64)
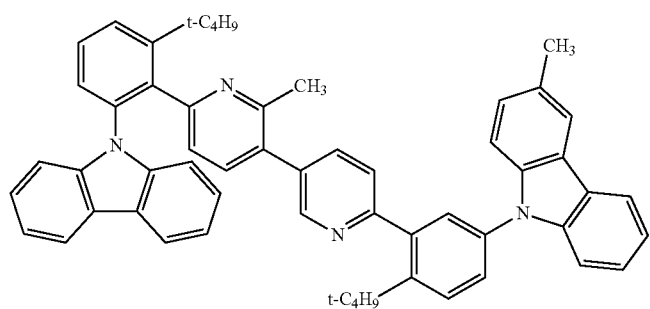

-continued
[Chem. 68]
(Compound 65)
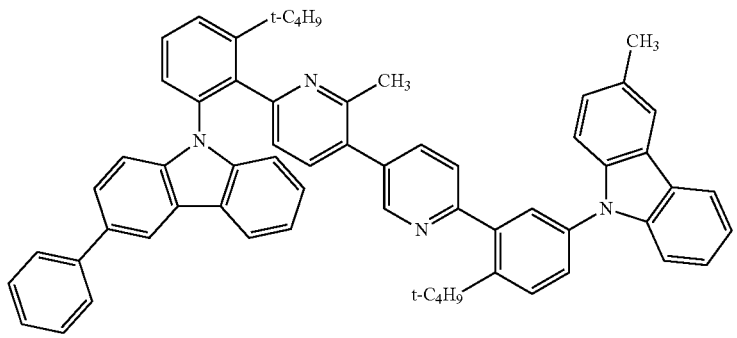
[Chem. 69]
(Compound 66)
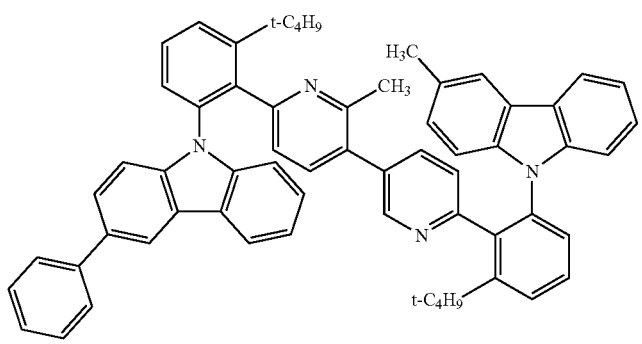
[Chem. 70]
(Compound 67)
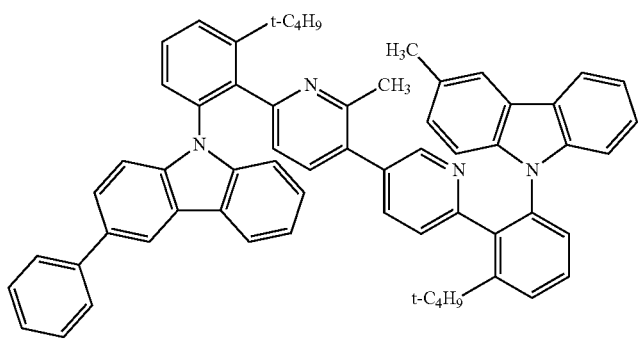
[Chem. 71]
(Compound 68)
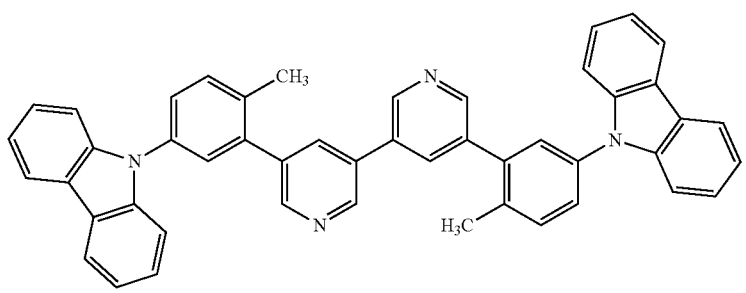

-continued
[Chem. 72]
(Compound 69)
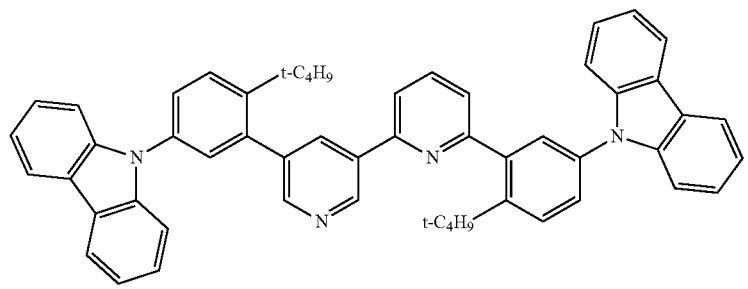
[Chem. 73]
(Compound 70)
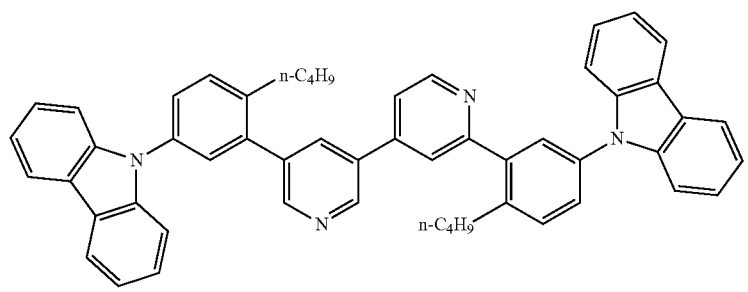
[Chem. 74]
(Compound 71)
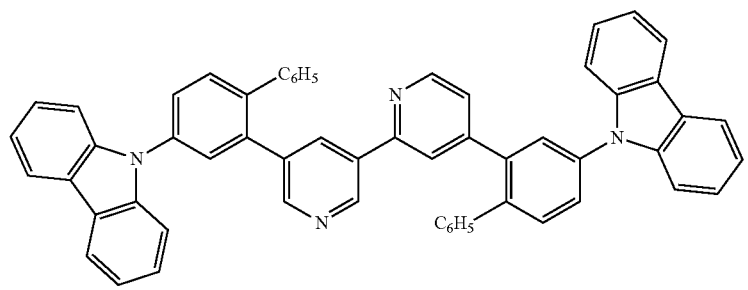
[Chem. 75]
(Compound 72)
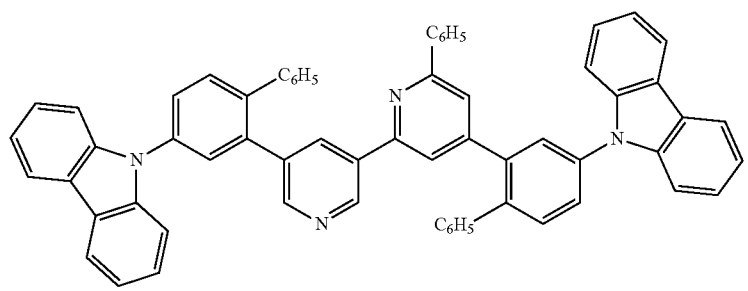

[Chem. 76]
(Compound 73)
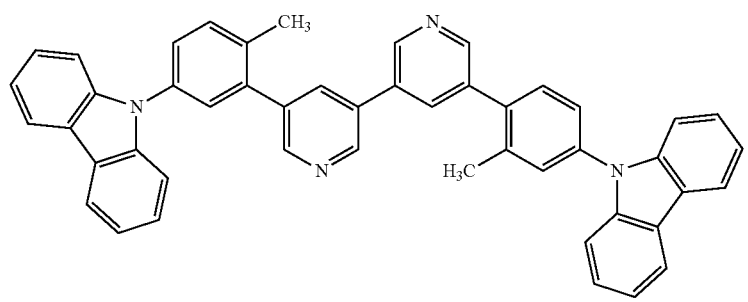
[Chem. 77]
(Compound 74)
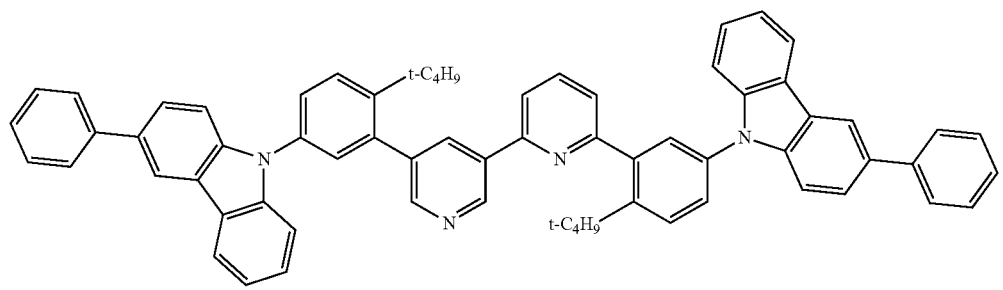
[Chem. 78]
(Compound 75)
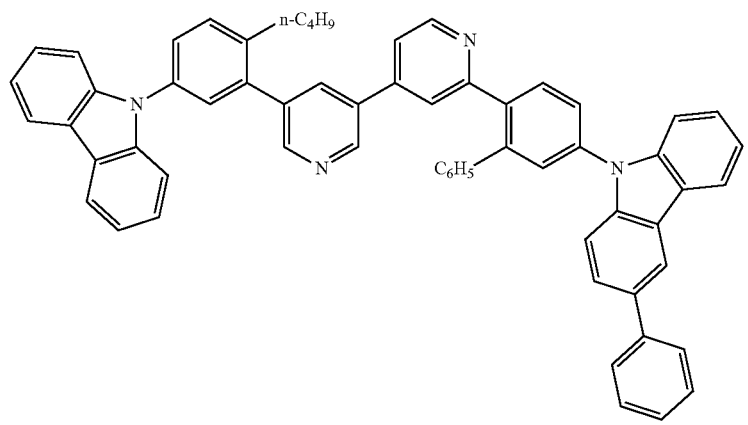
[Chem. 79]
(Compound 76)
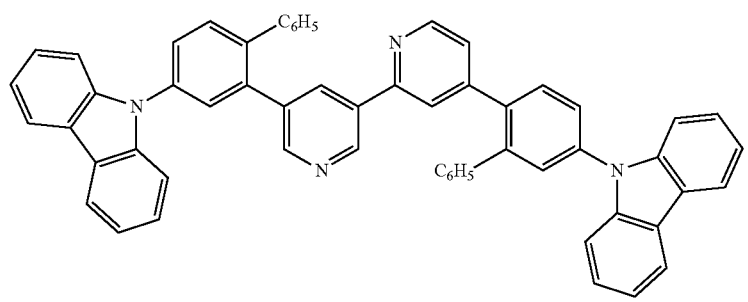

[Chem. 80]
(Compound 77)
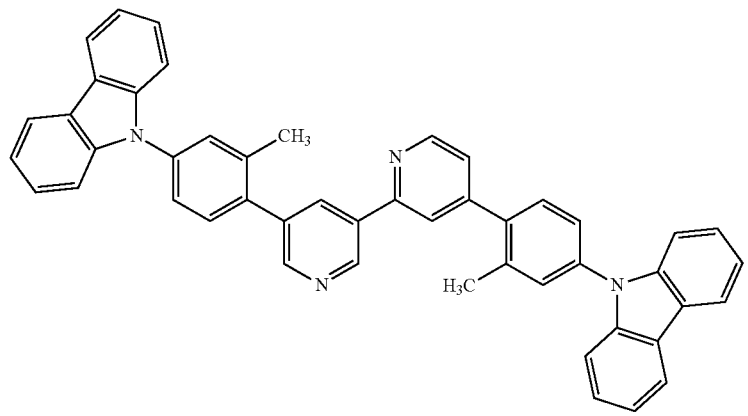
[Chem. 81]
(Compound 78)
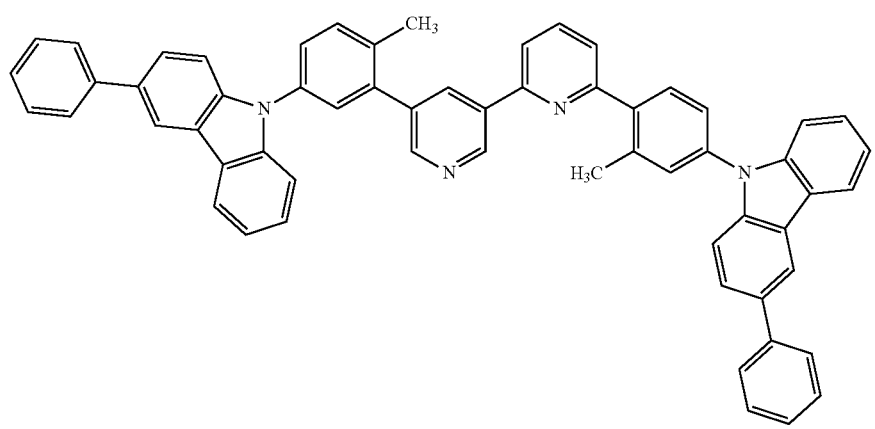
[Chem. 82]
(Compound 79)
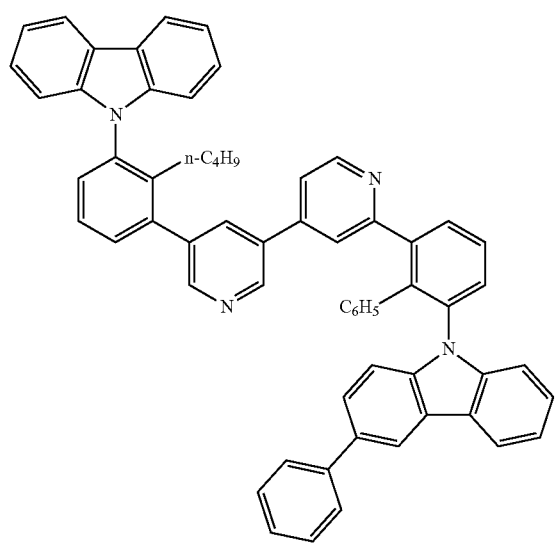

[Chem. 83]
(Compound 80)
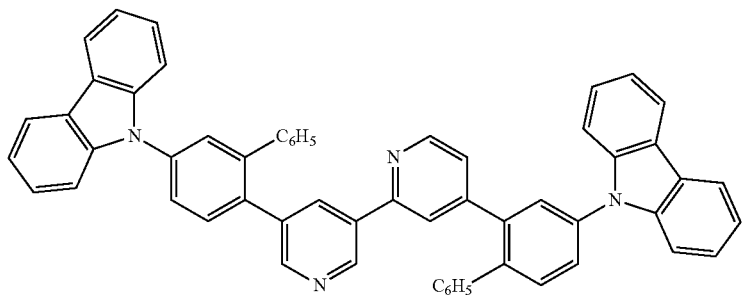
[Chem. 84]
(Compound 81)
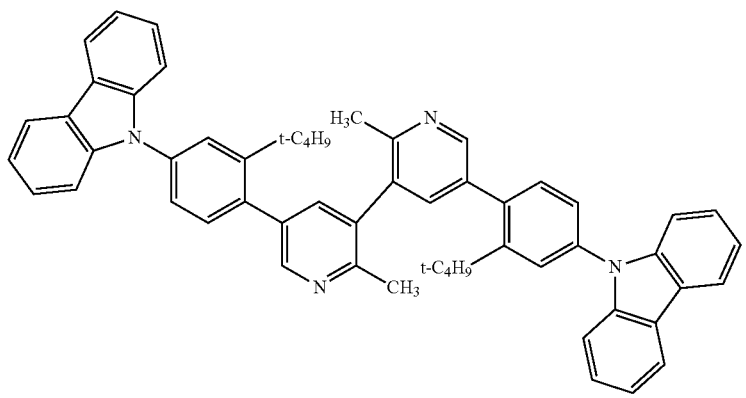
[Chem. 85]
(Compound 82)
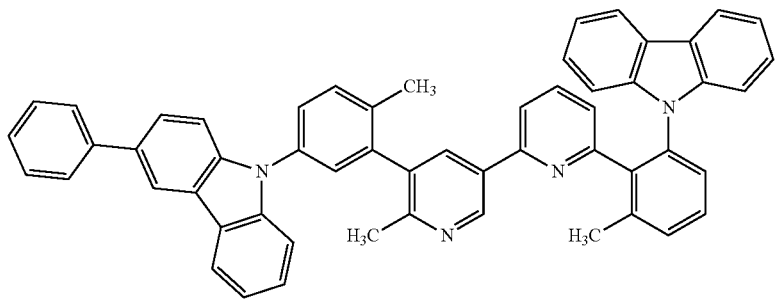

(Compound 83)
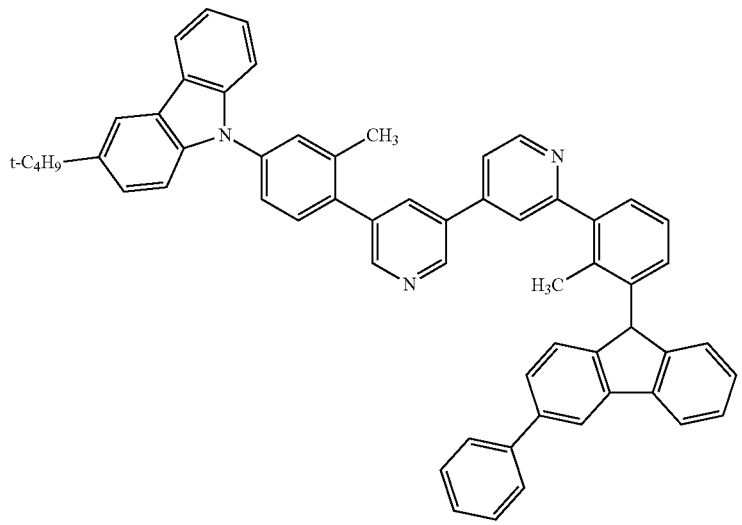
(Compound 84)
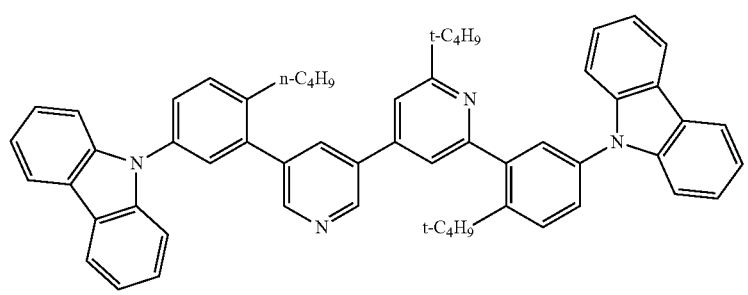
(Compound 85)
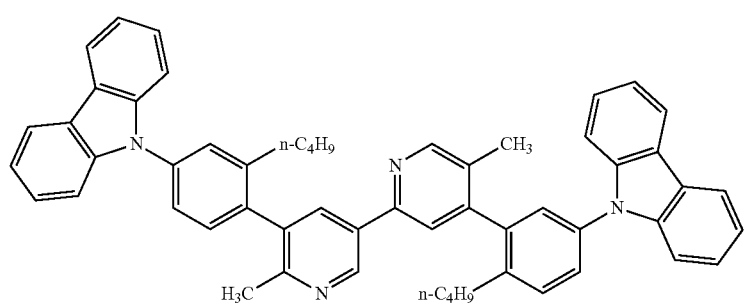
(Compound 86)
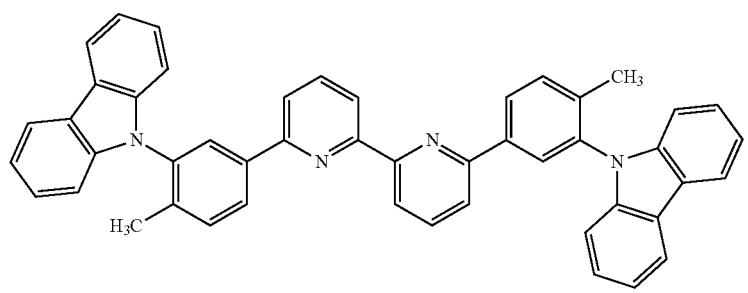

[Chem. 90]

(Compound 87)

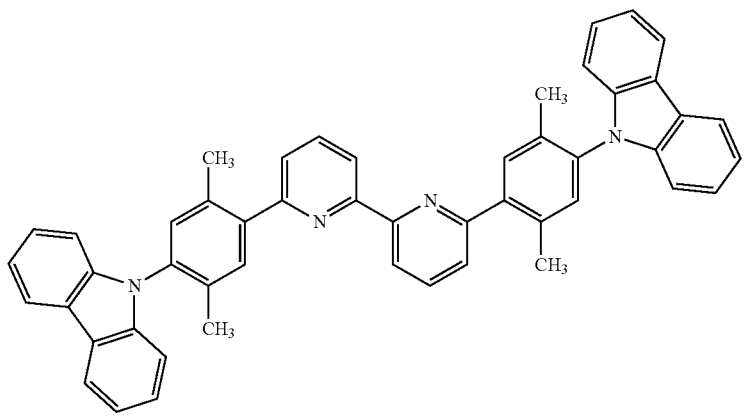

Purification of these compounds was performed through purification with column chromatography, adsorption purification with silica gel, activated charcoal, activated earth, or the like, recrystallization or crystallization from a solvent, or the like. Identification of these compounds was performed through NMR analysis. As physical properties, melting point, glass transition point (Tg), and work function were measured. The melting point serves as an indicator of vapor deposition properties; the glass transition point (Tg) serves as an indicator of stability in a thin film state; and the work function serves as an indicator of application to an emission host material.

The melting point and glass transition point (Tg) were measured using powders by means of a high-sensitivity differential scanning calorimeter ("DSC3100S", trade name; product of Bruker AXS).

The work function was measured using a 100-nm thick thin film of a sample formed on an ITO substrate by means of a photoelectron spectrophotometer in air ("AC-3", trade name; product of Riken Keiki Co., Ltd.).

The excited triplet level of the compound of the present invention can be calculated from a measured phosphorescence spectrum. The phosphorescence spectrum can be measured using a commercially available spectrophotometer. Examples of typical methods of measuring a phosphorescence spectrum include a method of dissolving a sample in a solvent and conducting measurement while irradiating excitation light thereto at a low temperature (refer to, for example, Non-patent Document 5), and a method of vapor-depositing a sample on a silicon substrate to form a thin film and then conducting measurement of a phosphorescence spectrum while irradiating excitation light thereto at a low temperature (refer to, for example, Patent Document 1). The excited triplet level can be calculated by reading the wavelength at the first peak of the phosphorescence spectrum on a short wavelength side or the wavelength at a rising position on the short wavelength side and converting it into a light energy value in accordance with the below equation. The excited triplet level serves as an indicator of confinement of triplet excitons of a phosphorescent emitter.

$$E(eV) = hc/\lambda \qquad \text{[Equation 1]}$$

Here, E represents a light energy value, h represents a Planck's constant ($6.63 \times 10^{-34}$ Js), c represents the light speed ($3.00 \times 10^8$ m/s), and $\lambda$ represents the wavelength (nm) at the rising position on the short wavelength side of a phosphorescence spectrum. Note that 1 eV corresponds to $1.60 \times 10^{-19}$ J.

As a structure of the organic EL element of the present invention, there may be mentioned one having, on a substrate, an anode, a hole-injection layer, a hole-transport layer, an electron-blocking layer, a light-emitting layer, a hole-blocking layer, an electron-transport layer, and a cathode in this order; and one further having, between the electron-transport layer and the cathode, an electron-injection layer. From these multilayer structures, some of the organic layers can be omitted and in such a case, it may be one having, on a substrate, an anode, a hole-transport layer, a light-emitting layer, an electron-transport layer, an electron-injection layer, and a cathode in this order; or one having an anode, a hole-transport layer, a light-emitting layer, an electron-transport layer, and a cathode in this order.

The light-emitting layer, the hole-transport layer, and the electron-transport layer each may have a stacked structure of two or more layers.

For the anode of the organic EL element of the present invention, use can be made of electrode materials having a large work function such as ITO and gold. For the hole-injection layer of the organic EL element of the present invention, use can be made of, in addition to porphyrin compounds typified by copper phthalocyanine, naphthalenediamine derivatives; starburst triphenylamine derivatives; triphenylamine trimers and tetramers such as arylamine compounds having, in the molecule thereof, a structure in which three or more triphenylamine structures have been connected through a single bond or a hetero-atom-free divalent group; acceptor type heterocyclic compounds such as hexacyanoazatriphenylene; application type polymer materials; and the like. These materials can be formed into a thin film by any known method such as spin coating or inkjet method, as well as vapor deposition.

For the hole-transport layer of the organic EL element of the present invention, use can be made of, in addition to compounds containing m-carbazolylphenyl group, benzidine derivatives such as N,N'-diphenyl-N,N'-di(m-tolyl)-benzidine (hereinafter abbreviated as TPD), N,N'-diphenyl-N,N'-di(α-naphthyl)-benzidine (hereinafter abbreviated as NPD), and N,N,N',N'-tetrabiphenylylbenzidine, 1,1-bis[(di-4-tolylamino)phenyl]cyclohexane (hereinafter abbreviated as TAPC), and various trimer of tetramer of triphenylamines, and the like. They may be formed into a film alone, may be used as a single layer formed after mixing with another material, or may be formed into a stacked structure of singly formed layers, of layers each formed after mixing, or of a singly formed layer and a layer formed after mixing. For the hole-injection/transport layer, also use can be made of an application type polymer material such as poly(3,4-ethylenedioxythiophene) (hereinafter abbreviated as PEDOT)/poly(styrene sulfonate) (hereinafter abbreviated as PSS). These materials can be formed into a thin film by any known method such as spin coating or inkjet method, as well as vapor deposition.

For the hole-injection layer or hole-transport layer, use can be made of a material, where a material ordinarily used for these layers is further P-doped with tristribromophenylamine hexachloroantimony; polymer compounds having, as a partial structure thereof, the structure of TPD; and the like.

For the electron-blocking layer of the organic EL element of the present invention, use can be made of compounds having an electron-blocking effect, for example, carbazole derivatives such as 4,4',4"-tri(N-carbazolyl)triphenylamine (hereinafter abbreviated as TCTA), 9,9-bis[4-(carbazole-9-yl)phenyl]fluorene, 1,3-bis(carbazole-9-yl)benzene (hereinafter abbreviated as mCP), 2,2-bis(4-carbazol-9-ylphenyl) adamantane (hereinafter abbreviated as "Ad-Cz"), and compounds having a triphenylsilyl group and a triarylamine structure typified by 9-[4-(carbazol-9-yl)phenyl]-9-[4-(triphenylsilyl)phenyl]-9H-fluorene. They may be formed into a film alone, may be used as a single layer formed after mixing with another material, or may be formed into a stacked structure of singly formed layers, of layers each formed after mixing, or of a singly formed layer and a layer formed after mixing. These materials can be formed into a thin film by any known method such as spin coating or inkjet method, as well as vapor deposition.

For the light-emitting layer of the organic EL element of the present invention, use can be made of, in addition to metal complexes of a quinolinol derivative including tris(8-hydroxyquioline)aluminum (hereinafter abbreviated as $Alq_3$), various metal complexes, anthracene derivatives, bisstyrylbenzene derivatives, pyrene derivatives, oxazole derivatives, and polyparaphenylene vinylene derivatives. Further, the light-emitting layer may be composed of a host material and a dopant material. As the host material, use can be made of the compound having a bipyridyl group and carbazole ring represented by the general formula (1) of the present invention, mCP, thiazole derivatives, benzimidazole derivatives, and polydialkylfluorene derivatives. As the dopant material, use can be made of quinacridone, coumarin, rubrene, anthracene, and perylene, and derivatives thereof, benzopyran derivatives, rhodamine derivatives, and aminostyryl derivatives. They may be formed into a film alone, may be used as a single layer formed after mixing with another material, or may be formed into a stacked structure of singly formed layers, of layers each formed after mixing, or of a singly formed layer and a layer formed after mixing.

As the light-emitting material, phosphorescent light-emitting materials can be used. As the phosphorescent emitter, phosphorescent light-emitting materials of metal complexes of iridium or platinum can be used. Green phosphorescent emitters such as $Ir(ppy)_3$, blue phosphorescent emitters such as FIrpic and FIr6, red phosphorescent emitters such as $Btp_2Ir(acac)$, and the like may be used. At this time, as a host material, use can be made of carbazole derivatives such as CBP, TCTA and mCP, or the like as a hole-injection/transporting host material, while as an electron-transporting host material, use can be made of p-bis(triphenylsilyl)benzene (hereinafter abbreviated as UGH2), 2,2',2"-(1,3,5-phenylene)-tris(1-phenyl-1H-benzimidazole) (hereinafter abbreviated as TPBI) or the like. Alternatively, the compound having a bipyridyl group and carbazole ring represented by the general formula (1) of the present invention may be used as the host material.

In order to avoid concentration quenching, the phosphorescent light-emitting material is doped into the host material preferably in a range of from 1 to 30 wt %, relative to the whole light-emitting layer, by using co-deposition.

These materials can be formed into a thin film by any known method such as spin coating or inkjet method, as well as vapor deposition.

It is also possible to fabricate an element having a structure where, on a light-emitting layer formed using the compound of the present invention, another light-emitting layer formed using a compound different in work function as a host material is stacked (refer to, for example, Non-patent Document 6).

For the hole-blocking layer of the organic EL element of the present invention, use can be made of, in addition to the compound having a bipyridyl group and carbazole ring represented by the general formula (1) of the present invention, compounds having a hole-blocking effect, for example, phenanthroline derivatives such as bathocuproine (hereinafter abbreviated as BCP), metal complexes of a quinolinol derivatives such as aluminum (III) bis(2-methyl-8-quinolinato)-4-phenylphenolate (hereinafter abbreviated as BAlq), various rare earth complexes, oxazole derivatives, triazole derivatives, and triazine derivatives. These materials may also serve as a material of the electron-transport layer. They may be formed into a film alone, may be used as a single layer formed after mixing with another material, or may be formed into a stacked structure of singly formed layers, of layers each formed after mixing, or of a singly formed layer and a layer formed after mixing. These materials can be formed into a thin film by any known method such as spin coating or inkjet method, as well as vapor deposition.

For the electron-transport layer of the organic EL element of the present invention, use can be made of, in addition to metal complexes of quinolinol derivatives such as $Alq_3$ and BAlq, various metal complexes, triazole derivatives, triazine derivatives, oxadiazole derivatives, thiadiazole derivatives, carbodiimide derivatives, quinoxaline derivatives, phenanthroline derivatives, silole derivatives, and the like. They may be formed into a film alone, may be used as a single layer formed after mixing with another material, or may be formed into a stacked structure of singly formed layers, of layers each formed after mixing, or of a singly formed layer and a layer formed after mixing. These materials can be formed into a thin film by any known method such as spin coating or inkjet method, as well as vapor deposition.

For the electron-injection layer of the organic EL element of the present invention, use can be made of alkali metal salts such as lithium fluoride and cesium fluoride, alkaline earth metal salts such as magnesium fluoride, metal oxides such as aluminum oxide, and the like, but in the case where the electron-transport layer and the cathode are preferably selected, it may be omitted.

Moreover, for the electron-injection layer or electron-transport layer, use can be made of a material, where a material ordinarily used for these layers is further N-doped with a metal such as cesium.

For the cathode of the organic EL element of the present invention, use can be made of electrode materials having a low work function such as aluminum, and alloys having a lower work function such as magnesium silver alloy, magnesium indium alloy, and aluminum magnesium alloy as the electrode material.

The embodiments of the present invention will hereinafter be described more specifically by Examples. However, the present invention is not limited by the following Examples.

EXAMPLE 1

Synthesis of 6,6'-bis[3-(9H-carbazol-9-yl)-6-methylphenyl]-2,2'-bipyridine (Compound 13)

To a reaction vessel purged with nitrogen were charged 50 g of 4-bromo-2-chlorotoluene, 48.8 g of carbazole, 7.7 g of a copper powder, 100.1 g of potassium carbonate, 5.2 ml of dimethyl sulfoxide, and 20 ml of dodecylbenzene, followed by heating, and stirred at 200° C. for 43 hours. After cooling to 80° C., thereto was added 350 ml of toluene, an insoluble matter was removed by filtration therefrom, and vacuum concentration was conducted to obtain a crude product. The crude product was purified by column chromatography (carrier: silica gel, eluent: hexane) to obtain 34.4 g (yield: 49%) of 9-(3-chloro-4-methylphenyl)-9H-carbazole as a white powder.

To a reaction vessel purged with nitrogen were charged 20.0 g of the resulting 9-(3-chloro-4-methylphenyl)-9H-carbazole, 10.1 g of potassium acetate, 19.2 g of bispinacolatodiboron, and 60 ml of 1,4-dioxane. Then, thereto were added 1.2 g of bis(dibenzylideneacetone) palladium and 1.4 g of tricyclohexylphosphine, followed by heating, and stirred at 90° C. for 72 hours. After cooling to room temperature, thereto was added 50 ml of water, and thereafter, thereto was added 100 ml of chloroform to separate it into layers. The organic layer was dried over magnesium sulfate and then subjected to vacuum concentration to obtain a crude product. The crude product was purified by recrystallization from 300 ml of methanol and then washed with 400 ml of hexane to obtain 9.3 g (yield: 36%) of 9-(4-methyl-3-pinacolatoboryl-phenyl)-9H-carbazole as a opaque-white solid.

To a reaction vessel purged with nitrogen were charged 8.0 g or the resulting 9-(4-methyl-3-pinacolatoboryl-phenyl)-9H-carbazole, 3.3 g of 6,6'-dibromo-2,2'-bipyridine, 31 ml of a 2M aqueous solution of potassium carbonate, 60 ml of toluene, 15 ml of ethanol, and 0.6 g of tetrakis(triphenylphosphine) palladium (0), followed by heating, and stirred at 72° C. for 7 hours. After cooling to room temperature, thereto was added 30 ml of methanol, and the crude product thus precipitated was collected by filtration. After the crude product was dissolved in 1200 ml of chloroform, adsorption purification was conducted using 12.7 g of silica gel. Vacuum concentration was conducted, and the obtained solid was washed with 30 ml of acetone and purified by crystallization using a toluene/methanol mixed solvent to obtain 3.34 g (yield: 49%) of 6,6'-bis[3-(9H-carbazol-9-yl)-6-methylphenyl]-2,2'-bipyridine (Compound 13) as a white powder.

The structure of the white powder thus obtained was identified using NMR. The $^1$H-NMR measurement result is shown in FIG. 1.

By $^1$H-NMR (CDCl$_3$), the following 34 hydrogen signals were detected. δ (ppm)=8.50 (2H), 8.15 (4H), 7.89 (2H), 7.77 (2H), 7.61-7.50 (10H), 7.43-7.41 (4H), 7.29 (4H), 2.64 (6H).

EXAMPLE 2

Synthesis of 6,6'-bis[3-(9H-carbazol-9-yl)-4-methylphenyl]-2,2'-bipyridine (Compound 86)

To a reaction vessel purged with nitrogen were charged 45 g of 2-bromo-4-chlorotoluene, 36.6 g of carbazole, 7.0 g of a copper powder, 90.8 g of potassium carbonate, 4.7 ml of dimethyl sulfoxide, and 25 ml of dodecylbenzene, followed by heating, and stirred at 200° C. for 44 hours. After cooling to 80° C., thereto was added 400 ml of toluene, an insoluble matter was removed by filtration therefrom, and vacuum concentration was conducted to obtain a crude product. Hexane was added to the crude product to precipitate the crude product. It was collected by filtration and then purified by column chromatography (carrier: silica gel, eluent: hexane) to obtain 20.3 g (yield: 32%) of 9-(3-chloro-6-methylphenyl)-9H-carbazole as a white powder.

To a reaction vessel purged with nitrogen were charged 17.3 g of the resulting 9-(3-chloro-6-methylphenyl)-9H-carbazole, 8.7 g of potassium acetate, 16.5 g of bispinacolatodiboron, and 50 ml of 1,4-dioxane. Then, thereto were added 1.0 g of bis(dibenzylideneacetone) palladium and 1.2 g of tricyclohexylphosphine, followed by heating, and stirred at 90° C. for 55 hours. After cooling to room temperature, thereto was added 40 ml of water, and thereafter, thereto was added 120 ml of chloroform to separate it into layers. The organic layer was dried over magnesium sulfate and then subjected to vacuum concentration to obtain a crude product. The crude product was purified by recrystallization from 200 ml of methanol and then washed with 400 ml of methanol to obtain 13.4 g (yield: 59%) of 9-(6-methyl-5-pinacolatoboryl-phenyl)-9H-carbazole as a gray solid.

To a reaction vessel purged with nitrogen were charged 8.0 g of the resulting 9-(6-methyl-5-pinacolatoboryl-phenyl)-9H-carbazole, 3.2 g of 6,6'-dibromo-2,2'-bipyridine, 30 ml of a 2M aqueous solution of potassium carbonate, 60 ml of toluene, 15 ml of ethanol, and 0.6 g of tetrakis(triphenylphosphine) palladium (0), followed by heating, and stirred at 72° C. for 4.5 hours. After cooling to room temperature, the crude product precipitated was collected by filtration. After the crude product was dissolved in 1400 ml of chloroform, adsorption purification was conducted using 21 g of NH silica gel. Vacuum concentration was conducted, and the obtained solid was washed with 60 ml of acetone to obtain 6.06 g (yield: 90%) of 6,6'-bis[3-(9H-carbazol-9-yl)-4-methylphenyl]-2,2'-bipyridine (Compound 86) as a white powder.

Figure 2:
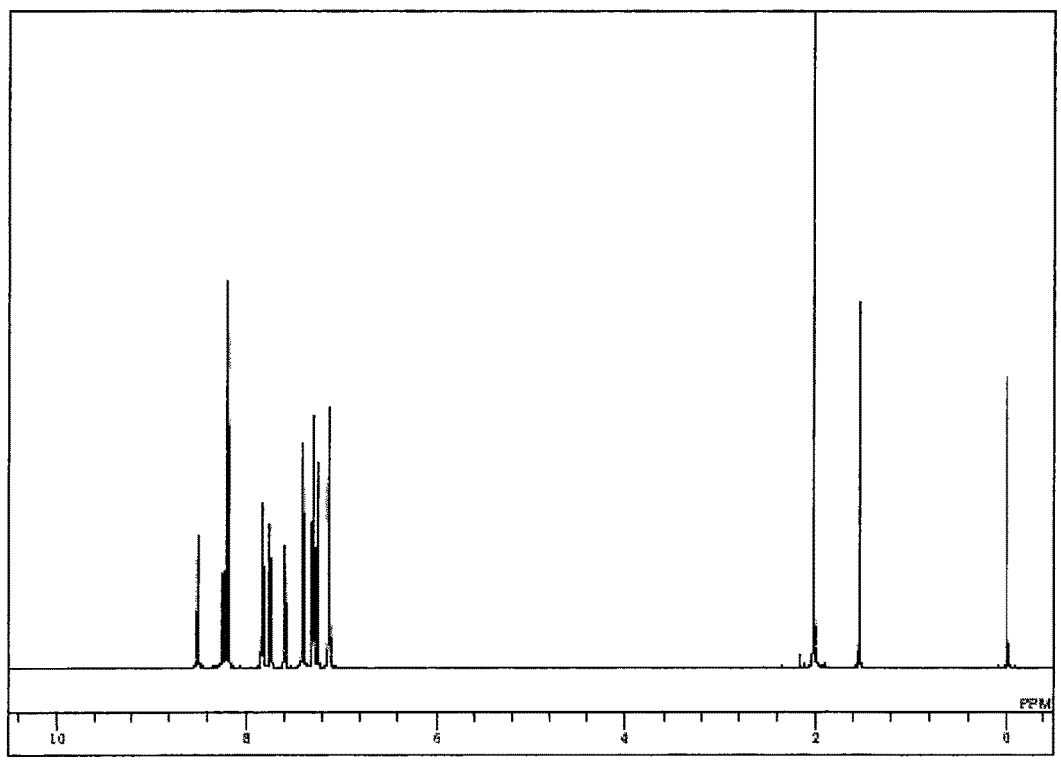
FIG. 2 is a $^1$H-NMR chart of the compound of Example 2 of the present invention (Compound 86).

The structure of the white powder thus obtained was identified using NMR. The $^1$H-NMR measurement result is shown in FIG. 2.

By $^1$H-NMR (CDCl$_3$), the following 34 hydrogen signals were detected. δ (ppm)=8.50 (2H), 8.25 (2H), 8.20 (6H), 7.83 (2H), 7.75 (2H), 7.60 (2H), 7.40 (4H), 7.29 (4H), 7.14 (4H), 2.03 (6H).

EXAMPLE 3

Synthesis of 6,6'-bis[4-(9H-carbazol-9-yl)-2,5-dimethylphenyl]-2,2'-bipyridine (Compound 87)

To a reaction vessel purged with nitrogen were charged 91.2 g of 2,5-dibromo-p-xylene, 38.5 g of carbazole, 7.3 g of a copper powder, 95.5 g of potassium carbonate, 5.5 ml of dimethyl sulfoxide, and 90 ml of dodecylbenzene, followed by heating, and stirred at 200° C. for 48 hours. After cooling to 80° C., thereto was added 250 ml of toluene, an insoluble matter was removed by filtration therefrom, and vacuum concentration was conducted to obtain a crude product. The crude product was purified by column chromatography (carrier: silica gel, eluent: hexane) to obtain 29.9 g (yield: 37%) of 9-(4-bromo-2,5-dimethylphenyl)-9H-carbazole as an amorphous solid.

To a reaction vessel purged with nitrogen were charged 28.1 g of the resulting 9-(4-bromo-2,5-dimethylphenyl)-9H-carbazole, 23.6 g of potassium acetate, 24.4 g of bispinacolatodiboron, and 700 ml of 1,4-dioxane. Then, thereto were added 3.9 g of [1,1'-bis(diphenylphosphino)ferrocene] palladium dichloride, followed by heating, and stirred at 90° C. for 24 hours. After cooling to room temperature, thereto was added 900 ml of aqueous sodium bisulfite, and thereafter, extraction operation using 500 ml of chloroform was conducted twice. The organic layers were combined, dried over magnesium sulfate, and then subjected to vacuum concentration to obtain a crude product. The crude product was purified by column chromatography (carrier: silica gel, eluent: hexane-toluene) to obtain 8.0 g (yield: 23%) of 9-(2,5-dimethyl-4-pinacolatoboryl-phenyl)-9H-carbazole as a gray solid.

To a reaction vessel purged with nitrogen were charged 8.0 g of the resulting 9-(2,5-dimethyl-4-pinacolatoboryl-phenyl)-9H-carbazole, 3.2 g of 6,6'-dibromo-2,2'-bipyridine, 30 ml of a 2M aqueous solution of potassium carbonate, 60 ml of toluene, 15 ml of ethanol, and 0.6 g of tetrakis(triphenylphosphine) palladium (0), followed by heating, and stirred at 72° C. for 4.5 hours. After cooling to room temperature, the crude product precipitated was collected by filtration. After the crude product was dissolved in 1400 ml of chloroform, adsorption purification was conducted using 21 g of NH silica gel. Vacuum concentration was conducted, and the obtained solid was washed with 60 ml of acetone to obtain 5.40 g (yield: 77%) of 6,6'-bis[4-(9H-carbazol-9-yl)-2,5-dimethylphenyl]-2,2'-bipyridine (Compound 87) as a white powder.

Figure 3:
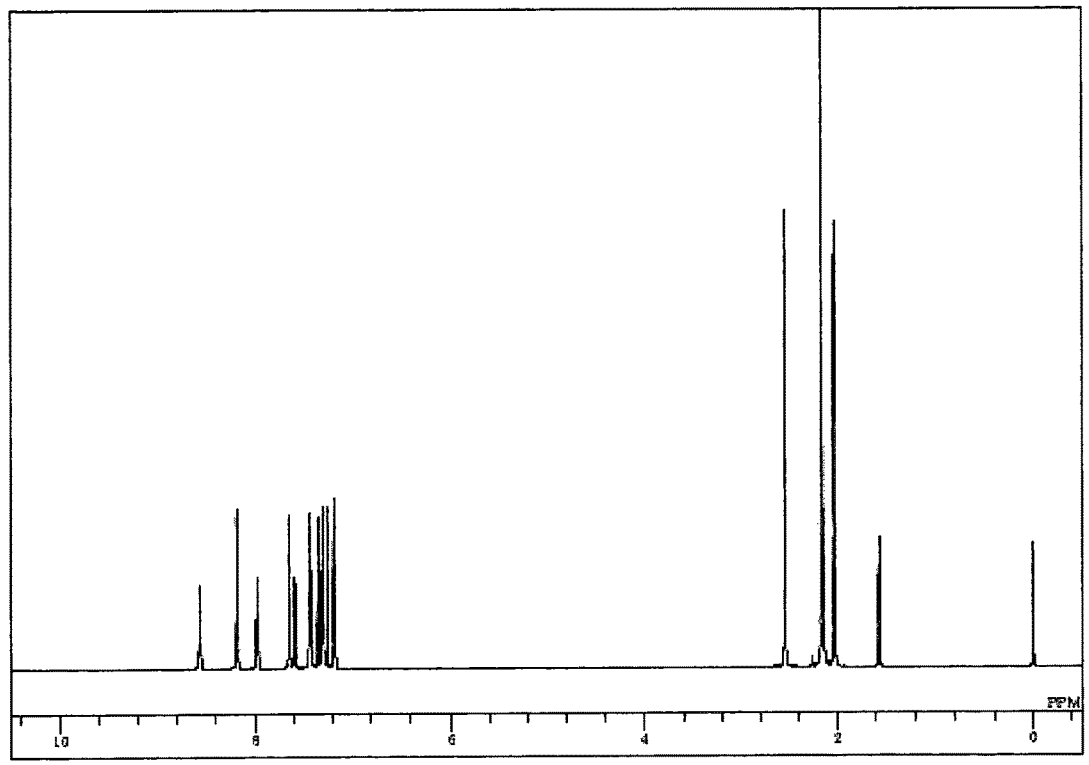
FIG. 3 is a $^1$H-NMR chart of the compound of Example 3 of the present invention (Compound 87).

The structure of the white powder thus obtained was identified using NMR. The $^1$H-NMR measurement result is shown in FIG. 3.

By $^1$H-NMR (CDCl$_3$), the following 38 hydrogen signals were detected. δ (ppm)=8.57 (2H), 8.18 (4H), 7.97 (2H), 7.64 (2H), 7.60 (2H), 7.43 (4H), 7.35 (2H), 7.31 (4H), 7.18 (4H), 2.54 (6H), 2.04 (6H).

EXAMPLE 4

The glass transition point of the compounds of the present invention was determined by using a high-sensitivity differential scanning calorimeter ("DSC3100S", trade name; product of Bruker AXS).

|  | Glass transition point |
| --- | --- |
| Compound of Invention Example 1 | 132° C. |
| Compound of Invention Example 2 | 134° C. |
| Compound of Invention Example 3 | 159° C. |
| mCP | 55° C. |

The compounds of the present invention have a glass transition point of 100° C. or higher. This suggests that the compounds of the present invention are stable in a thin film state.

EXAMPLE 5

A deposited film having a thickness of 100 nm was formed on an ITO substrate by using the compounds of the present invention and their work function was measured by using a photoelectron spectrophotometer in air ("AC-3", trade name; product of Riken Keiki Co., Ltd.)

|  | Work function |
| --- | --- |
| Compound of Invention Example 1 | 5.87 eV |
| Compound of Invention Example 2 | 5.89 eV |
| Compound of Invention Example 3 | 6.01 eV |
| CBP | 6.00 eV |

Thus, the compounds of the present invention show a preferable energy level compared with that of CBP ordinarily used as an emission host.

EXAMPLE 6

Regarding the compound of the present invention, a $1.0 \times 10^{-5}$ mol/L solution of 2-methyltetrahydrofuran was prepared. The solution thus prepared was put into a quartz tube for exclusive use, fed with pure nitrogen to remove oxygen, and then, further sealed with a rubber septum to prevent oxygen from entering. After cooling to 77K, a phosphorescence spectrum was measured by irradiating excitation light by using a spectrometer ("FluoroMax-4", trade name; product of Horiba, Ltd.). The wavelength at a rising position on the short wavelength side of the phosphorescence spectrum was read and converted the wavelength value into light energy, and an excited triplet level was calculated therefrom.

|  | Excited triplet level |
| --- | --- |
| Compound of Invention Example 1 | 2.84 eV |
| Compound of Invention Example 2 | 2.79 eV |
| Compound of Invention Example 3 | 2.85 eV |
| CBP | 2.57 eV |
| FIrpic | 2.67 eV |

Thus, the compounds of the present invention have triplet energy levels higher than those of FIrpic or CBP which is an ordinarily-employed blue phosphorescent material, and have the ability of sufficiently confining the triplet energy excited in the light-emitting layer.

EXAMPLE 7

Figure 4:
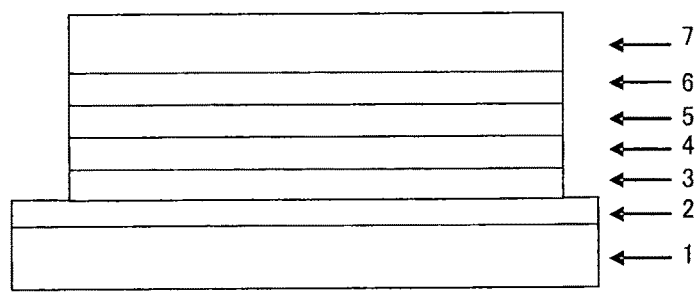
FIG. 4 is a figure showing the constitution of EL elements of Example 7 and Comparative Example 1.

An organic EL element was fabricated, as shown in FIG. 4, by vapor depositing a hole-transport layer 3, a light-emitting layer 4, an electron-transport layer 5, an electron-injection layer 6, and a cathode (aluminum electrode) 7 in this order on an ITO electrode formed in advance as a transparent anode 2 on a glass substrate 1.

More specifically, after washing, with an organic solvent, the glass substrate 1, on which an ITO having a thickness of 150 nm had been formed, the surface thereof was washed further by oxygen plasma processing. Then, the resulting glass substrate with the ITO electrode was installed in a vacuum vapor deposition apparatus and the pressure was reduced to 0.001 Pa or less.

Next, TAPC was formed as the hole-transport layer 3 at a deposition rate of 1.0 Å/sec so as to cover the ITO electrode (transparent anode 2) and to have a thickness of 40 nm. On the hole-transport layer 3, the compound of Invention Example 1 (Compound 13) and FIrpic which is a blue phosphorescent emitter were formed as the light-emitting layer 4 by binary vapor deposition at a deposition rate where the deposition rate ratio of the compound of Invention Example 1 (Compound 13):FIrpic was 94:6, so as to have a film thickness of 30 nm. On the light-emitting layer 4, the TPBI was formed at a deposition rate of 1.0 Å/sec as the electron-transport layer 5, so as to have a film thickness of 40 nm. On the electron-transport layer 5, lithium fluoride was formed at a deposition rate of 0.1 Å/sec as the electron-injection layer 6, so as to have a film thickness of 0.5 nm. Finally, aluminum was vapor-deposited so as to have a film thickness of 150 nm, to form the cathode 7. The organic EL element thus fabricated was subjected to a property measurement at normal temperature in the atmosphere.

Measurement results of emission properties obtained by applying a DC voltage to the organic EL element fabricated by using the compound of Example 1 of the present invention (Compound 13) are shown collectively in Table 1.

COMPARATIVE EXAMPLE 1

For comparison, an organic EL element was fabricated under conditions similar to those employed in Example 7 except that, as materials of the light-emitting layer 4 in Example 7, the mCP and FIrpic which is a blue phosphorescent emitter were formed by binary vapor deposition at a deposition rate where the deposition rate ratio of mCP:FIrpic was 94:6 so as to have a film thickness of 30 nm. The organic EL element thus fabricated was subjected to a property measurement at normal temperature in the atmosphere.

Measurement results of emission properties obtained by applying a DC voltage to the organic EL element thus fabricated are shown collectively in Table 1.

TABLE 1

| Compound | Voltage [V] (@10 mA/cm$^2$) | Brightness [cd/m$^2$] (@10 mA/cm$^2$) | Emission efficiency [cd/A] (@10 mA/cm$^2$) | Power efficiency [lm/W] (@10 mA/cm$^2$) |
|---|---|---|---|---|
| Ex. 7 Compound 10 | 5.92 | 1741 | 17.63 | 9.35 |
| Comp. Ex. 1 mCP | 6.88 | 1789 | 18.28 | 8.31 |

As shown in Table 1, when an electric current having a current density of 10 mA/cm$^2$ was passed therethrough, a driving voltage became a lower voltage as 5.92V in the case of the compound of Invention Example 1 (Compound 13) as compared with 6.88V in the case of mCP. In addition, when an electric current having a current density of 10 mA/cm$^2$ was passed therethrough, a power efficiency was remarkably improved.

As described above, the compounds of the present invention have a high excited triplet level; smoothly transmit energy to a phosphorescent emitter and completely confine the triplet excitons of the phosphorescent emitter; and moreover show good thin-film stability, so that they are excellent as host compounds of the light-emitting layer.

While the present invention has been described in detail and referring to specific embodiments, it is apparent for those skilled in the art that various modifications or changes can be made without departing from the spirit and scope of the present invention.

The present application is based on Japanese Patent Application No. 2011-039406 filed on Feb. 25, 2011, and the contents thereof are incorporated herein by reference.

INDUSTRIAL APPLICABILITY

The compound having a bipyridyl group and carbazole ring of the present invention have a high excited triplet level, can completely confine the triplet excitons of the phosphorescent emitter, and have good thin-film stability, so that they are excellent as a host compound of a light-emitting layer and as a hole-blocking compound. Moreover, organic EL elements fabricated using the compounds have markedly improved brightness and emission efficiency compared with conventional organic EL elements, so that they can improve the performance of mobile electronic products.

DESCRIPTION OF REFERENCE NUMERALS AND SIGNS

1. Glass substrate
2. Transparent electrode
3. Hole-transport layer
4. Light-emitting layer
5. Electron-transport layer
6. Electron-injection layer
7. Cathode

The invention claimed is:

1. A compound represented by formula (2):

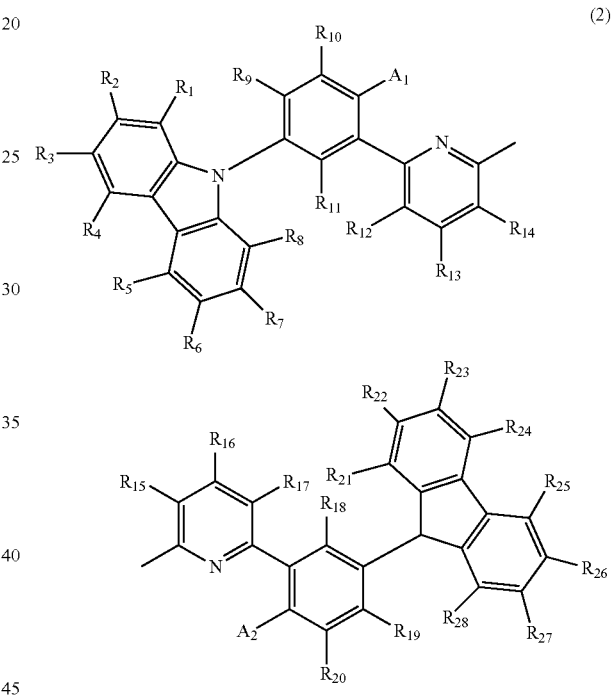

wherein:
$A_1$ and $A_2$ each independently represent a cyano group, a nitro group, a linear or branched alkyl group having from 1 to 6 carbon atoms, a linear or branched alkoxy group having from 1 to 6 carbon atoms, a trifluoromethyl group, or a substituted or unsubstituted aromatic hydrocarbon group; and $R_1$ to $R_{28}$ each independently represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.

2. An organic electroluminescent element comprising a pair of electrodes and at least one organic layer interposed between the electrodes, wherein the organic layer comprises the compound of claim 1.

3. The organic etectroluminescent element of claim 2, wherein the organic layer is a light-emitting layer.

4. The organic electroluminescent element of claim 2, wherein the organic layer is a hole-blocking layer.

5. An organic electroluminescent element comprising:
a pair of electrodes; and
a light-emitting layer between the electrodes;
wherein the light-emitting layer comprises a phosphorescent light-emitting material and the compound of claim 1.

6. The organic electroluminescent element of claim 2, further comprising a light-emitting layer comprising a phosphorescent light-emitting material.

7. The organic electroluminescent element of claim 6, wherein the organic layer is a hole-blocking layer.

8. The organic electroluminescent element of claim 5, wherein the phosphorescent light-emitting material is a metal complex comprising iridium or platinum.

9. The organic electroluminescent element of claim 6, wherein the phosphorescent light-emitting material is a metal complex comprising iridium or platinum.

10. The organic electroluminescent element of claim 7, wherein the phosphorescent light-emitting material is a metal complex comprising iridium or platinum.

11. The organic electroluminescent element of claim 8, wherein the phosphorescent light-emitting material is a metal complex comprising iridium.

12. The organic electroluminescent element of claim 8, wherein the phosphorescent light-emitting material is a metal complex comprising platinum.

13. The organic electroluminescent element of claim 9, wherein the phosphorescent light-emitting material is a metal complex comprising iridium.

14. The organic electroluminescent element of claim 9, wherein the phosphorescent light-emitting material is a metal complex comprising platinum.

15. The organic electroluminescent element of claim 10, wherein the phosphorescent light-emitting material is a metal complex comprising iridium.

16. The organic electroluminescent element of claim 10, wherein the phosphorescent light-emitting material is a metal complex comprising platinum.

17. A compound represented by formula (2):

wherein:
$A_1$ and $A_2$ each independently represent a cyano group, a nitro group, a linear or branched alkoxy group having from 1 to 6 carbon atoms, a trifluoromethyl group, or a substituted or unsubstituted aromatic hydrocarbon group; and $R_1$ to $R_{28}$ each independently represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.

18. An organic electroluminescent element comprising a pair of electrodes and at least one organic layer interposed between the electrodes, wherein the organic layer comprises the compound of claim 17.

19. The organic electroluminescent element of claim 18, wherein the organic layer is a light-emitting layer.

20. The organic electroluminescent element of claim 18, wherein the organic layer is a hole-blocking layer.

21. An organic electroluminescent element comprising:
a pair of electrodes; and
a light-emitting layer between the electrodes;
wherein the light-emitting layer comprises a phosphorescent light-emitting material and the compound of claim 17.

22. The organic electroluminescent element of claim 18, further comprising a light-emitting layer comprising a phosphorescent light-emitting material.

23. The organic electroluminescent element of claim 22, wherein the organic layer is a hole-blocking layer.

24. The organic electroluminescent element of claim 21, wherein the phosphorescent light-emitting material is a metal complex comprising iridium or platinum.

25. The organic electroluminescent element of claim 22, wherein the phosphorescent light-emitting material is a metal complex comprising iridium or platinum.

26. The organic electroluminescent element of claim 23, wherein the phosphorescent light-emitting material is a metal complex comprising iridium or platinum.

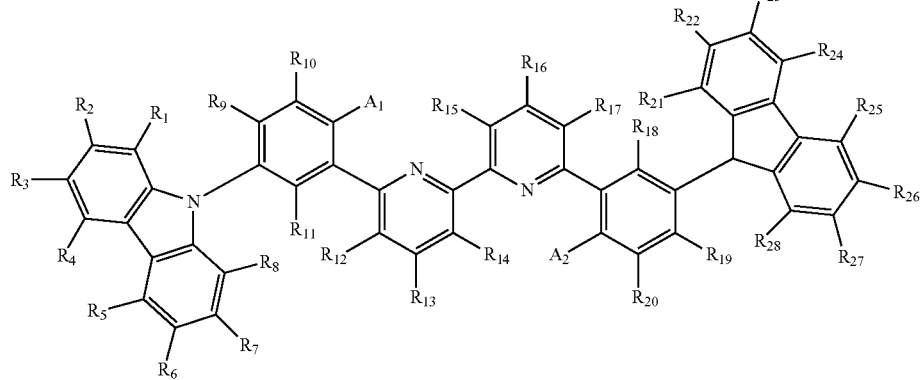

27. The organic electroluminescent element of claim 24, wherein the phosphorescent light-emitting material is a metal complex comprising iridium.

28. The organic electroluminescent element of claim 24, wherein the phosphorescent light-emitting material is a metal complex comprising platinum.

29. The organic electroluminescent element of claim 25, wherein the phosphorescent light-emitting material is a metal complex comprising iridium.

30. The organic electroluminescent element of claim 25, wherein the phosphorescent light-emitting material is a metal complex comprising platinum.

31. The organic electroluminescent element of claim 26, wherein the phosphorescent light-emitting material is a metal complex comprising iridium.

32. The organic electroluminescent element of claim 26, wherein the phosphorescent light-emitting material is a metal complex comprising platinum.

33. A compound represented by formula (3):

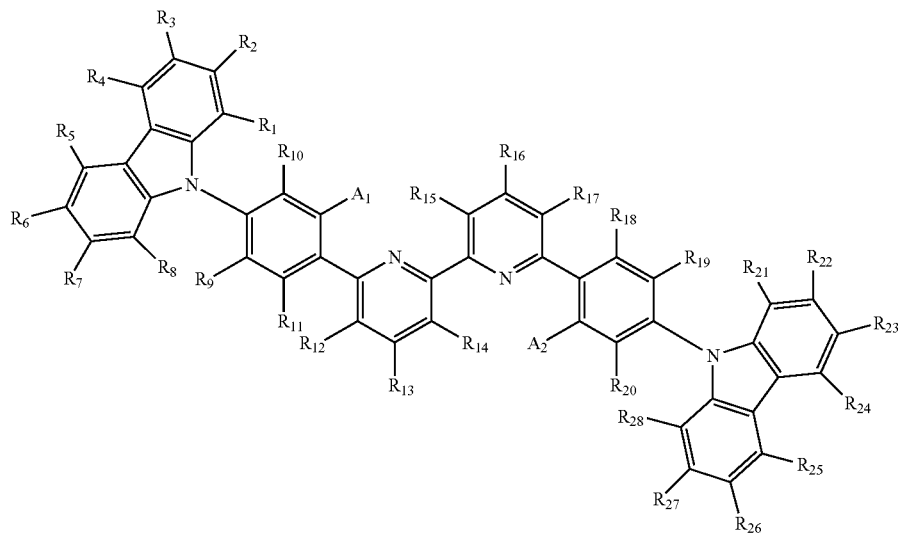

(3)

wherein:
$A_1$ and $A_2$ each independently represent a cyano group, a nitro group, a linear or branched alkyl group having from 1 to 6 carbon atoms, a linear or branched alkoxy group having from 1 to 6 carbon atoms, a trifluoromethyl group, or a substituted or unsubstituted aromatic hydrocarbon group; and $R_1$ to $R_{28}$ each independently represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.

34. An organic electroluminescent element comprising a pair of electrodes and at least one organic layer interposed between the electrodes, wherein the organic layer comprises the compound of claim 33.

35. The organic electroluminescent element of claim 34, wherein the organic layer is a light-emitting layer.

36. The organic electroluminescent element of claim 34, wherein the organic layer is a hole-blocking layer.

37. An organic electroluminescent element comprising:
a pair of electrodes; and
a light-emitting layer between the electrodes;
wherein the light-emitting layer comprises a phosphorescent light-emitting material and the compound of claim 33.

38. The organic electroluminescent element of claim 34, further comprising a light-emitting layer comprising a phosphorescent light-emitting material.

39. The organic electroluminescent element of claim 38, wherein the organic layer is a hole-blocking layer.

40. The organic electroluminescent element of claim 37, wherein the phosphorescent light-emitting material is a metal complex comprising iridium or platinum.

41. The organic electroluminescent element of claim 38, wherein the phosphorescent light-emitting material is a metal complex comprising iridium or platinum.

42. The organic electroluminescent element of claim 39, Wherein the phosphorescent light-emitting material is a metal complex comprising iridium or platinum.

43. The organic electroluminescent element of claim 40, wherein the phosphorescent light-emitting material is a metal complex comprising iridium.

44. The organic electroluminescent element of claim 40, wherein the phosphorescent light-emitting material is a metal complex comprising platinum.

45. The organic electroluminescent element of claim 41, wherein the phosphorescent light-emitting material is a metal complex comprising iridium.

46. The organic electroluminescent element of claim 41, wherein the phosphorescent light-emitting material is a metal complex comprising platinum.

47. The organic electroluminescent element of claim 42, wherein the phosphorescent light-emitting material is a metal complex comprising iridium.

48. The organic electroluminescent element of claim 42, wherein the phosphorescent light-emitting material is a metal complex comprising platinum.

49. A compound represented by formula (3):

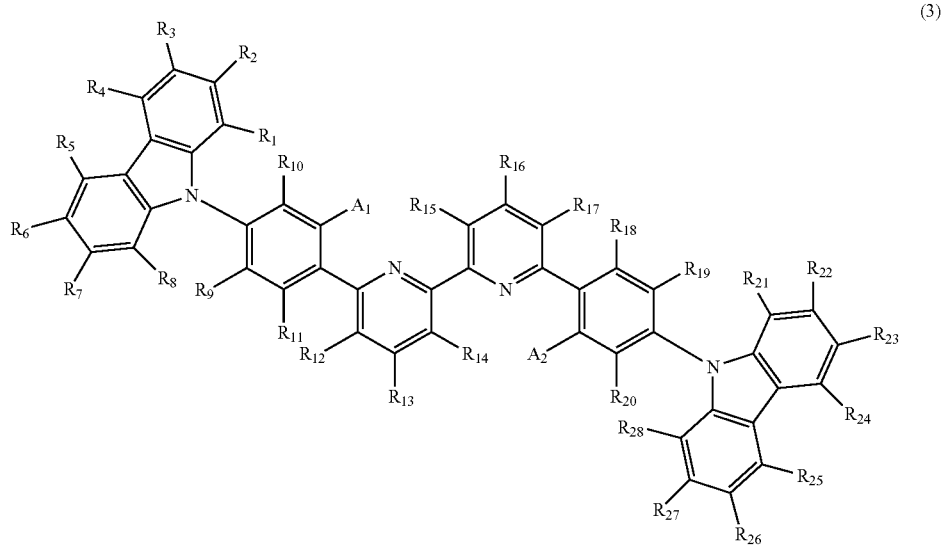

wherein:
$A_1$ and $A_2$ each independently represent a cyano group, a nitro group, a linear or branched alkoxy group having from 1 to 6 carbon atoms, a trifluoromethyl group, or a substituted or unsubstituted aromatic hydrocarbon group; and $R_1$ to $R_{28}$ each independently represent a hydrogen atom, a deuterium atom, a fluorine atom, a chlorine atom, a cyano group, a nitro group, a linear or branched alkyl group having from 1 to 6 carbon atoms, a linear or branched alkoxy group having from 1 to 6 carbon atoms, a trifluoromethyl group, a substituted or unsubstituted aromatic hydrocarbon group, a substituted or unsubstituted aromatic heterocyclic group, or a substituted or unsubstituted condensed polycyclic aromatic group.

50. An organic electroluminescent element comprising a pair of electrodes and at least one organic layer interposed between the electrodes, wherein the organic layer comprises the compound of claim 49.

51. The organic electroluminescent element of claim 50, wherein the organic layer is a light-emitting layer.

52. The organic electroluminescent element of claim 50, wherein the organic layer is a hole-blocking layer.

53. An organic electroluminescent element comprising:
a pair of electrodes; and
a light-emitting layer between the electrodes;
wherein the light-emitting layer comprises a phosphorescent light-emitting material and the compound of claim 49.

54. The organic electroluminescent element of claim 50, further comprising a light-emitting layer comprising a phosphorescent light-emitting material.

55. The organic electroluminescent element of claim 54, wherein the organic layer is a hole-blocking layer.

56. The organic electroluminescent element of claim 53, wherein the phosphorescent light-emitting material is a metal complex comprising iridium or platinum.

57. The organic electroluminescent element of claim 54, wherein the phosphorescent light-emitting material is a metal complex comprising iridium or platinum.

58. The organic electroluminescent element of claim 55, Wherein the phosphorescent light-emitting material is a metal complex comprising iridium or platinum.

59. The organic electroluminescent element of claim 56, wherein the phosphorescent light-emitting material is a metal complex comprising iridium.

60. The organic electroluminescent element of claim 56, wherein the phosphorescent light-emitting material is a metal complex comprising platinum.

61. The organic electroluminescent element of claim 57, wherein the phosphorescent light-emitting material is a metal complex comprising iridium.

62. The organic electroluminescent element of claim 57, wherein the phosphorescent light-emitting material is a metal complex comprising platinum.

63. The organic electroluminescent element of claim 58, wherein the phosphorescent light-emitting material is a metal complex comprising iridium.

64. The organic electroluminescent element of claim 58, wherein the phosphorescent light-emitting material is a metal complex comprising platinum.

* * * * *